United States Patent
O'Hara et al.

(10) Patent No.: US 11,622,980 B2
(45) Date of Patent: Apr. 11, 2023

(54) COMPOSITIONS COMPRISING PREBIOTICS AND PROBIOTICS

(71) Applicant: OPTIBIOTIX LIMITED, York (GB)

(72) Inventors: Stephen O'Hara, York (GB); Sofia Kolida, York (GB)

(73) Assignee: OPTIBIOTIX LIMITED, York (GB)

( * ) Notice: Subject to any disclaimer, the term of this patent is extended or adjusted under 35 U.S.C. 154(b) by 0 days.

(21) Appl. No.: 16/766,026

(22) PCT Filed: Nov. 23, 2018

(86) PCT No.: PCT/GB2018/053402
§ 371 (c)(1),
(2) Date: May 21, 2020

(87) PCT Pub. No.: WO2019/102218
PCT Pub. Date: May 31, 2019

(65) Prior Publication Data
US 2020/0297785 A1    Sep. 24, 2020

(30) Foreign Application Priority Data

Nov. 23, 2017    (GB) ........................................ 1719480

(51) Int. Cl.
*C12N 1/20*    (2006.01)
*A61K 35/747*    (2015.01)
(Continued)

(52) U.S. Cl.
CPC .......... *A61K 35/747* (2013.01); *A23L 33/125* (2016.08); *A23L 33/135* (2016.08);
(Continued)

(58) Field of Classification Search
CPC ..................................................... C12N 1/20
See application file for complete search history.

(56) References Cited

U.S. PATENT DOCUMENTS

| | | |
|---|---|---|
| 2004/0005677 A1 | 1/2004 | Eddington |
| 2013/0330299 A1 | 12/2013 | Ranganathan |
| 2017/0106029 A1* | 4/2017 | Ranganathan ....... A61K 35/742 |

FOREIGN PATENT DOCUMENTS

| | | | | |
|---|---|---|---|---|
| CN | 107242351 A | 10/2017 | | |
| JP | 2005008616 A | 1/2005 | | |
| WO | WO-2011018547 A1 * | 2/2011 | ............ | A61K 35/74 |

OTHER PUBLICATIONS

International Search Report and Written Opinion corresponding to PCT/GB2018/053402, dated Jun. 27, 2019, 24 pages.
(Continued)

*Primary Examiner* — Rosanne Kosson
(74) *Attorney, Agent, or Firm* — Nicholas P. Stadnyk; Nexsen Pruet, PLLC

(57) ABSTRACT

The present invention relates to a *Lactobacillus* spp. selective prebiotic composition comprising one, or a mixture of two or more, of: xylooligosaccharides, cellobiose and/or gentiooligosaccharides. The present invention also relates to a synbiotic composition comprising a probiotic component comprising one or more strains of *Lactobacillus rhamnosus* and/or one or more strains of *Lactobacillus plantarum* and a prebiotic component comprising a growth medium which is specific for the growth of the probiotic component, wherein the prebiotic growth medium comprises one or more, or a mixture of two of more, components selected from: xylooligosaccharides, cellobiose and/or gentiooligosaccharides. The present invention also relates to methods of producing and selecting such compositions.

9 Claims, 39 Drawing Sheets
Specification includes a Sequence Listing.

(51) Int. Cl.
| | |
|---|---|
| A23L 33/24 | (2016.01) |
| A23L 33/125 | (2016.01) |
| A23L 33/135 | (2016.01) |
| A61K 47/26 | (2006.01) |
| A61K 47/38 | (2006.01) |
| A61K 9/00 | (2006.01) |
| A61K 9/14 | (2006.01) |
| A61K 9/20 | (2006.01) |
| A61K 9/48 | (2006.01) |

(52) U.S. Cl.
CPC .............. *A23L 33/24* (2016.08); *A61K 47/26* (2013.01); *A61K 47/38* (2013.01); *C12N 1/20* (2013.01); *A23Y 2220/67* (2013.01); *A23Y 2220/73* (2013.01); *A61K 9/009* (2013.01); *A61K 9/0095* (2013.01); *A61K 9/14* (2013.01); *A61K 9/20* (2013.01); *A61K 9/48* (2013.01); *C12N 2500/34* (2013.01)

(56) References Cited

OTHER PUBLICATIONS

Maria, Anani Eva et al., Gene expression of enzymes involved in utilization of xylooligosaccharides by Lactobacillusstrains, Biotechnology & Biotechnological Equipment, Diagnosis Press, Sofia, BG, vol. 28, No. 5, Sep. 3, 2014 (Sep. 3, 2014), pp. 941-948, XP009511267.

Yu, Xiuhua et al., Prebiotic Potential of Xylooligosaccharides Derived from Corn Cobs and Their In Vitro Antioxidant Activity When Combined with Lactobacillus, Journal of Microbiology and Biotechnology, Korean Society for Applied Microbiology, Seoul, KR, vol. 25, No. 7, Jun. 30, 2015 (Jun. 30, 2015), pp. 1084-1092, XP009511266.

Chunchai, Titikorn et al., Prebiotics, Probiotics or Synbiotics Therapy Restores Cognitive Decline in Obese Rats, Alzheimer's & Dementia: The Journal of the Alzheimer's Association, vol. 13, No. 7, Jul. 1, 2017 (Jul. 1, 2017), XP085217651.

Li, Zhaoping et al., In vitro study of the prebiotic xylooligosaccharide (XOS) on the growth of *Bifidobacterium* spp and *Lactobacillus* spp, International Journal of Food Sciences and Nutrition, Carfax Publishing Ltd, GB, vol. 66, No. 8, Nov. 17, 2015 (Nov. 17, 2015), pp. 919-922, XP009511262.

Celebioglu, Hasan Ufuk et al., Mucin- and carbohydrate-stimulated adhesion and subproteome changes of the probiotic bacteriumLactobacillus acidophilusNCFM, Journal of Proteomics, Elsevier, Amsterdam, NL, vol. 163, May 19, 2017 (May 19, 2017), pp. 102-110, XP085062526.

Umeki, Miki et al., Effect of Lactobacillusrhamnosus KY-3 and cellobiose as synbiotics on lipid metabolism in rats, Journal of Nutritional Science and Vitaminology, University of Tokyo Press, Tokyo, JP, vol. 50, No. 5, Sep. 30, 2004 (Sep. 30, 2004), pp. 330-334, XP009511206.

Holt, S M et al., Growth of various intestinal bacteria on alternansucrase-derived oligosaccharides, Letters in Applied Microbiology, Wiley-Blackwell Publishing Ltd, GB, vol. 40, No. 5, May 1, 2005 (May 1, 2005), pp. 385-390, XP009513775.

Anas, Mami et al., Screening of autochthonous *Lactobacillus* species from Algerian raw goats' milk for the production of bacteriocin-like compounds against *Staphylococcus aureus*, African Journal of Biotechnology, Academic Journals, Nairobi, Kenya, [Online] vol. 11, No. 20, Mar. 8, 2012 (Mar. 8, 2012), pp. 4595-4606, XP009513778.

Van Zanten, Gabriella C. et al., The effect of selected synbiotics on microbial composition and short-chain fatty acid production in a model system of the human colon, Plos One, Public Library of Science, US, vol. 7, No. 10, Jan. 1, 2012 (Jan. 1, 2012), pp. e47212-l, XP009513777.

\* cited by examiner

Figure 13 cont.
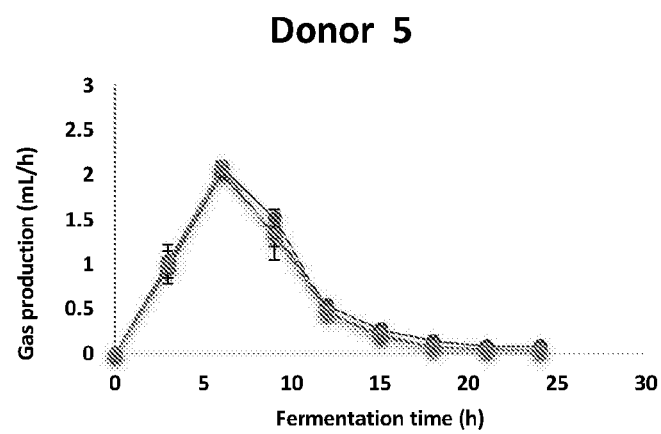
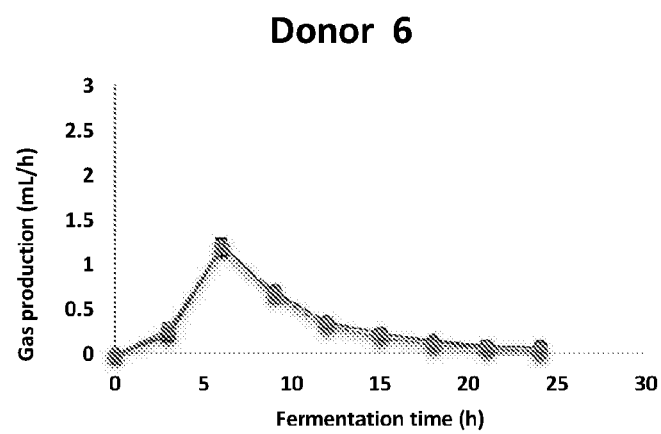
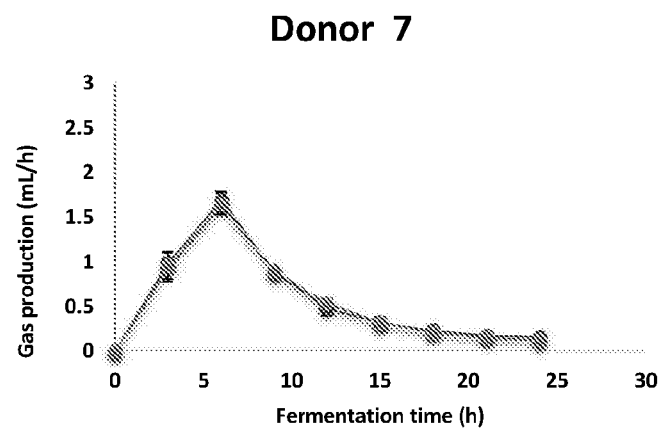

Figure 14
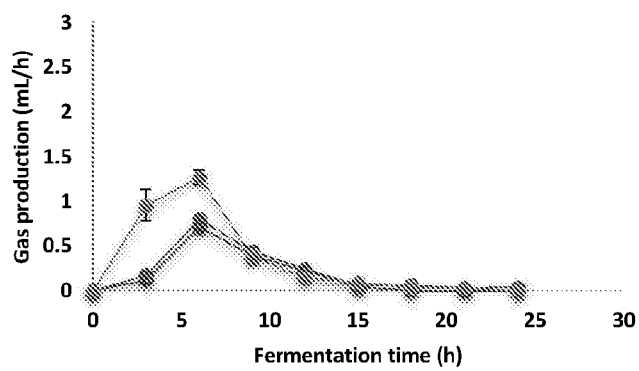
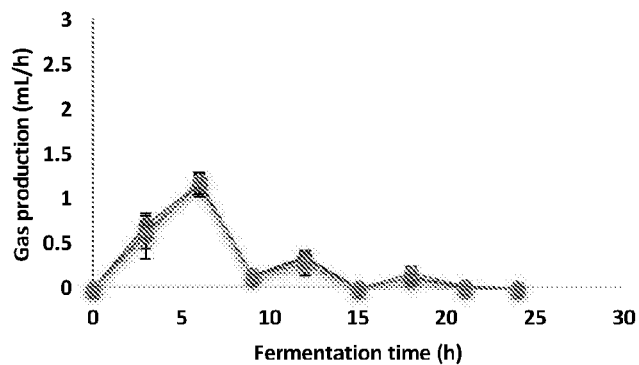
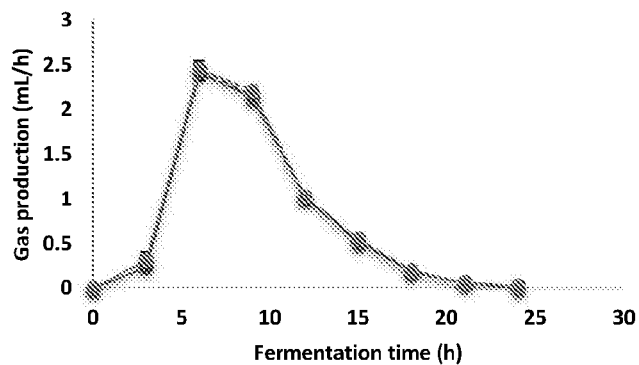

Figure 14 cont.
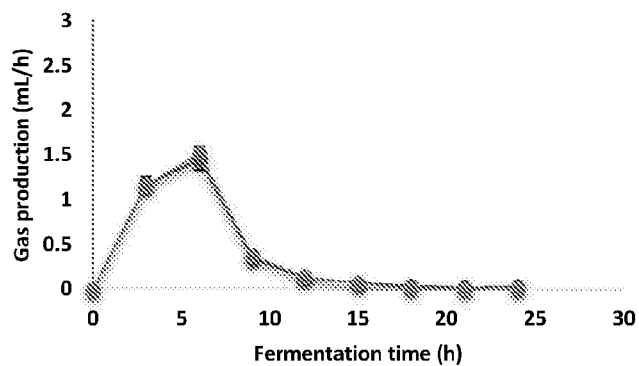
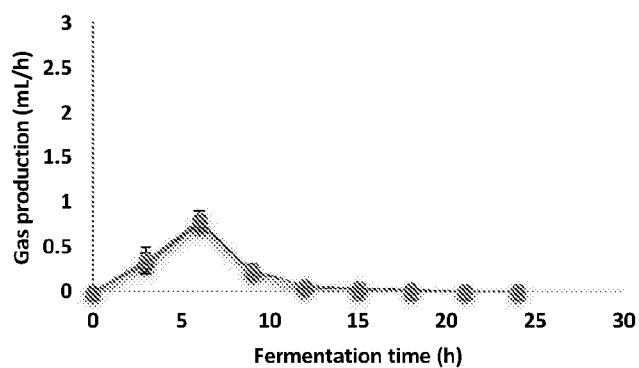
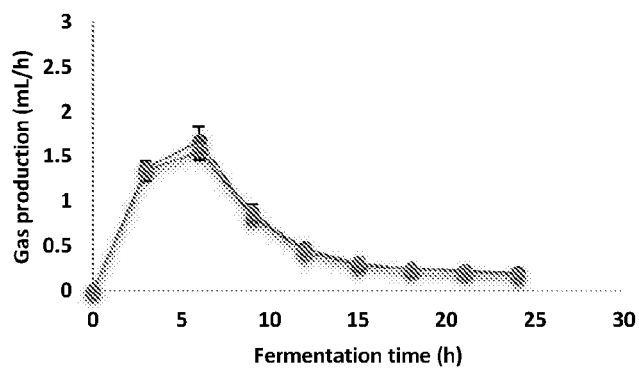

Figure 15 cont.
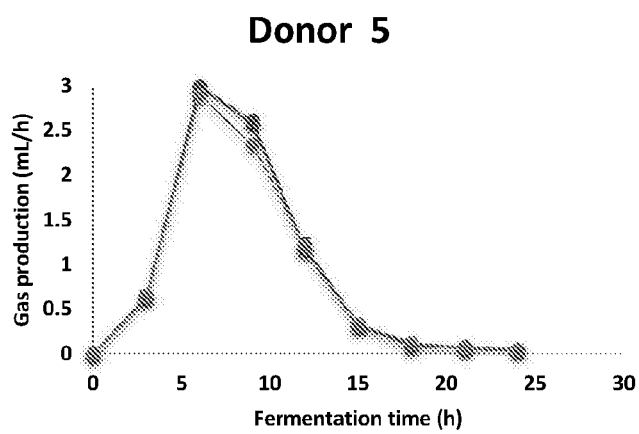
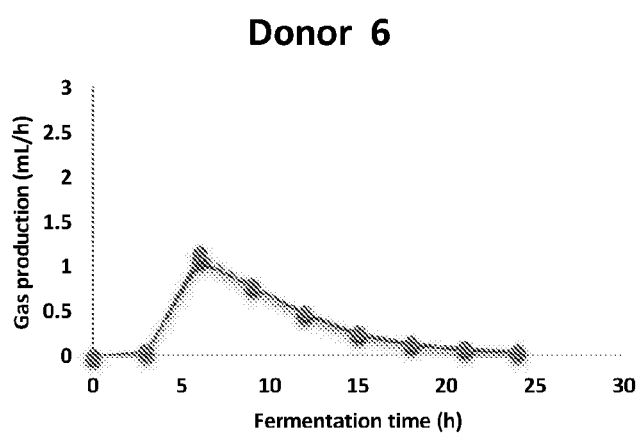
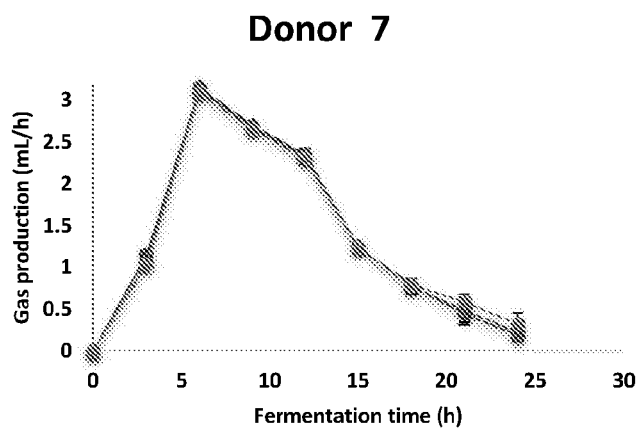

Figure 16
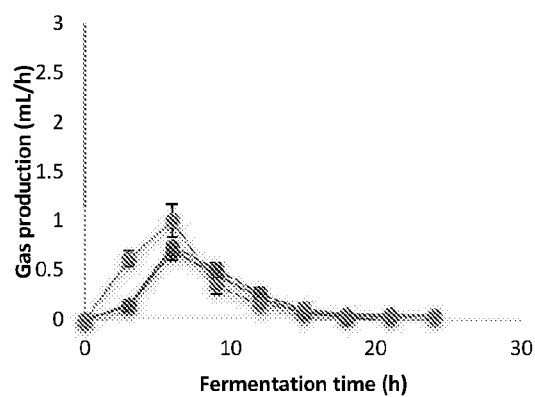
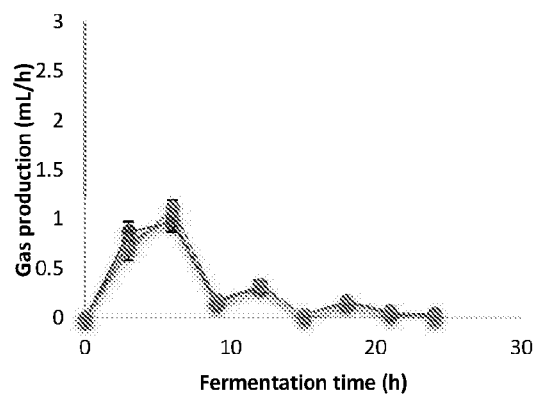
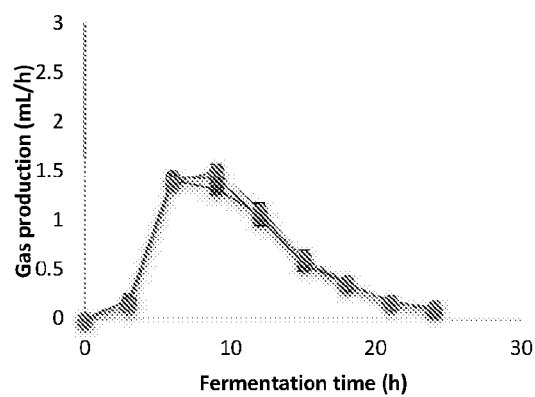

Figure 16 cont.
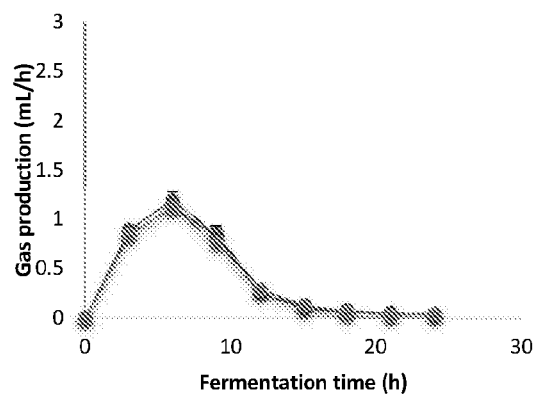
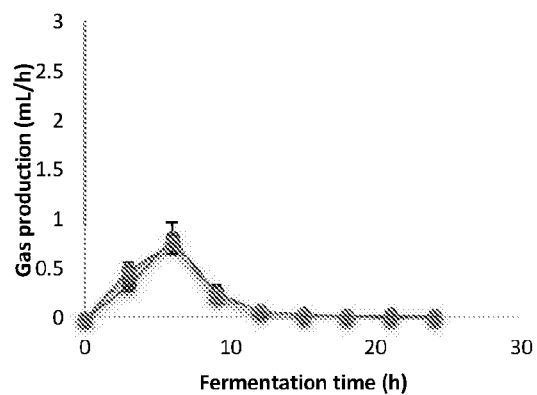
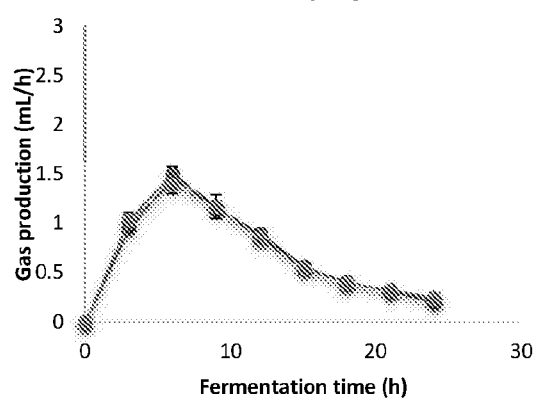

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: LR Forward primer

<400> SEQUENCE: 1
gcccttaaca gcagtcttc                                                      19

<210> SEQ ID NO 2
<211> LENGTH: 20
<212> TYPE: DNA
<213> ORGANISM: Artificial Sequence
<220> FEATURE:
<223> OTHER INFORMATION: LR Reverse primer

<400> SEQUENCE: 2
gccctccgta tgcttaaacc                                                     20

<210> SEQ ID NO 3
<211> LENGTH: 19
<212> TYPE: DNA
<213> ORGANISM: Artificial Sequence
<220> FEATURE:
<223> OTHER INFORMATION: LR Probe

<400> SEQUENCE: 3
tgttgatcaa tcagaggat                                                      19

COMPOSITIONS COMPRISING PREBIOTICS AND PROBIOTICS

CROSS-REFERENCE TO RELATED APPLICATIONS

This application is a U.S. national stage application under 35 U.S.C. § 371 of International Application No. PCT/GB2018/053402, filed Nov. 23, 2018, which claims priority to Great Britain Patent Application No. 1719480.4, filed Nov. 23, 2017, each of which is hereby incorporated by reference in its entirety.

TECHNICAL FIELD OF THE INVENTION

The invention relates to a *Lactobacillus* spp. selective prebiotic composition comprising one, or a mixture of two or more, of: xylooligosaccharides, cellobiose and/or gentiooligosaccharides. The invention also relates to a targeted synbiotic composition comprising said prebiotic composition and a *Lactobacillus*.

BACKGROUND TO THE INVENTION

Probiotics are bacteria which confer health benefits to a host. Typically, cultures of probiotic bacterial strains are consumed or administered to individuals in order to add to and augment naturally occurring, health positive bacterial populations in the gut. A number of health benefits have been associated with probiotics, including reducing the incidence of cancer, diarrhoea and irritable bowel syndrome, anti-pathogen activity to name a few. Preliminary studies also indicate that probiotics can be useful in reducing serum levels of cholesterol and blood pressure and help modulate diabetes.

Prebiotics are substrates that are selectively utilized by host microorganisms, such as lactobacilli or bifidobacteria, conferring a health benefit, and are finding much increased application into the food sector. Prebiotics can be non digestible food ingredients that are selectively metabolised by colonic bacteria which contribute to improved health. As such, their use can promote beneficial changes within the indigenous gut microbial milieu and they can help survivability of probiotics. They are distinct from most dietary fibres like pectin, celluloses, xylan, which have a global effect on gut bacterial populations and are not selectively metabolised in the gut. Criteria for classification as a prebiotic is that it must resist gastric acidity, hydrolysis by mammalian enzymes and gastrointestinal absorption, and it reaches the colon in appropriate amount to be fermented by intestinal microflora and selectively stimulate the growth and/or activity of intestinal bacteria associated with health and well-being.

Synbiotics are mixtures of probiotics and prebiotics that beneficially affect the host by improving the survival and implantation of probiotics in the gastrointestinal tract, by stimulating the growth and/or by activating the metabolism of one or a limited number of health-promoting bacteria, thus improving host welfare. A product containing oligofructose prebiotic and bifidobacteria probiotic could be considered to be a synbiotic if the mixture benefitted the host. Only a few synbiotics products are currently known and there is very little information on the selectivity of prebiotics on individual species. The ability to selectively increase the growth rate of an individual species or genus of bacteria without impacting on other bacterial groups creates the potential for targeted modulation of the microbiome and the potential to prevent, manage, or treat a number of human diseases.

It is an object of the present invention to provide a *Lactobacillus* spp. selective prebiotic. It is further an object of the present invention to provide a *L. rhamnosus* or a *L. plantarum* selective prebiotic which can be used as part of a synbiotic composition or synbiotic regime. It is also an object of the present invention to provide a novel synbiotic, whereby the prebiotic component can be used to specifically enhance the growth and activity of a *Lactobacillus* spp., such as *L. rhamnosus* strain or a *L. plantarum* strain probiotic component in vivo so as to confer one or more host benefits.

SUMMARY OF THE INVENTION

In accordance with a first aspect of the present invention, there is provided a *Lactobacillus* spp. selective prebiotic composition comprising one, or a mixture of two or more, of: xylooligosaccharides, cellobiose and/or gentiooligosaccharides.

The *Lactobacillus* spp. may comprise one or more strains of *L. rhamnosus*, such as *L. rhamnosus* GG and/or *L. rhamnosus* ATCC 53103. *L. rhamnosus* ATCC53103 or LGG®, is a strain which is manufactured and sold by Chr. Hansen A/S, Boege Allé 10-12, 2970 Hoersholm, Denmark and also commercially and freely available for purchase directly from ATCC on the www.LGCstandards-atcc.org website. Alternatively (or additionally) the *Lactobacillus* spp. may comprise (or further comprise) one or more strains of *Lactobacillus plantarum*, such as *Lactobacillus plantarum* 2830 (ECGC 13110402).

The composition may be formulated so as to be consumed or administered in conjunction with, or in combination with a *Lactobacillus* spp. probiotic component and thus forming a synbiotic. In one embodiment, the composition is formulated so as to be consumed or administered in conjunction with, or in combination with, one or more strains of *Lactobacillus* spp. at the same time. In other embodiments, the composition is formulated so as to be consumed or administered in conjunction with, or in combination with, one or more strains of *Lactobacillus* spp. sequentially, or separately. The consumption or administration may be such so as to pre-seed the gut of an individual with the one or more strains of *Lactobacillus* spp. (such as *L. rhamnosus* GG and/or *L. rhamnosus* ATCC 53103 and/or *Lactobacillus plantarum* 2830 (ECGC 13110402) and then feed the seeded strains with the prebiotic composition.

In one embodiment, the composition is in the form of one or more capsules, tablets, or sachets. The composition may be in the form of a capsule or tablet and/or components (such as the *Lactobacillus*) may be in the form of a capsule or tablet too. In an alternative embodiment, the composition may be in the form of an ingestible or drinkable liquid and/or powder format and/or can be mixed with a solid or liquid food stuff. Furthermore, the composition and/or *Lactobacillus* may be in the form of a drinkable liquid and/or powder format and/or can be mixed with a solid or liquid food stuff. The skilled addressee will appreciate that the composition may be in any format used to deliver nutrition or therapeutic products to the gut of an individual. For example, the composition may be in a powdered format in a sachet which is dispensed into the mouth without any liquid. Such products are often sold as a 'melt' in certain jurisdictions. The skilled addressee will also appreciate that the composition may also include other ingredients, such as flavours or preservatives.

The composition may be for use in increasing the population of *Lactobacillus* (or one or more selected strains thereof) in the gut of an individual. Such a population may be the indigenous population of the individual.

In a second, but related, aspect of the present invention, there is provided a synbiotic composition comprising a probiotic component comprising one or more strains of *Lactobacillus* spp. The one or more strains of *Lactobacillus* spp. may be one or more strains of *Lactobacillus rhamnosus* and/or one or more strains of *Lactobacillus plantarum* and a prebiotic component comprising a growth medium which is specific for the growth of the probiotic component, wherein the prebiotic growth medium comprises one or more, or a mixture of two or more, components selected from: xylooligosaccharides, cellobiose and/or gentiooligosaccharides.

In the synbiotic composition, the one or more strains of *L. rhamnosus* may comprise *L. rhamnosus* GG and/or *L. rhamnosus* ATCC 53103 and the one or more strains of *L. plantarum* may comprise *Lactobacillus plantarum* 2830 (ECGC 13110402).

The composition or growth medium may comprise up to about 3 g, up to about 2 g, up to about 1.75 g, up to about 1.5 g, up to about 1.25 g or up to about 1 g of the one or more, or mixture of two or more, xylooligosaccharides, cellobiose and/or gentiooligosaccharides. The composition or growth medium may comprise a daily dose of up to about 3 g, up to about 2 g, up to about 1.75 g, up to about 1.5 g, up to about 1.25 g or up to about 1 g of the one or more, or mixture of two or more, xylooligosaccharides, cellobiose and/or gentiooligosaccharides.

The composition or growth medium may comprise up to about 3 g, up to about 2 g, up to about 1.75 g, up to about 1.5 g, up to about 1.25 g or up to about 1 g of xylooligosaccharides. The composition or growth medium may comprise a daily dose of up to about 3 g, up to about 2 g, up to about 1.75 g, up to about 1.5 g, up to about 1.25 g or up to about 1 g of xylooligosaccharides.

The composition or growth medium may comprise up to about 20 g, up to about 17 g, up to about 15 g, up to about 12 g or up to about 8 g of the one or a mixture of cellobiose and/or gentiooligosaccharides. The composition or growth medium may comprise a daily dose of up to about 20 g, up to about 17 g, up to about 15 g, up to about 12 g or up to about 8 g of one or a mixture of cellobiose and/or gentiooligosaccharides.

The *Lactobacillus* may be in an amount in the range of $10^5$ cfu/g to $10^{12}$ cfu/g. More preferably, *Lactobacillus* may be in an amount in the range of $10^8$ cfu/g to $10^9$ cfu/g. The *Lactobacillus* may be in a daily dose of an amount in the range of $10^5$ cfu/g to $10^{12}$ cfu/g or in the range of $10^8$ cfu/g to $10^9$ cfu/g. It will be appreciated that the "cfu" refers to colony forming units which is a standard measure of bacterial cell quantity.

In certain embodiments of the synbiotic composition, *Lactobacillus* and/or the growth medium may be encapsulated or presented as a tablet. Furthermore, the growth medium may be used to encapsulate the *Lactobacillus*. The synbiotic composition may further comprise an excipient or carrier compound to enable the *Lactobacillus* and/or growth medium to pass through the gastrointestinal environment of the body or allow for timely delivery in different parts of the intestinal tract. Many encapsulation techniques will be apparent to the skilled addressee and the one employed will be tailored to the required stability of the prebiotic growth medium and/or *Lactobacillus* and desired digestive transit time. If the growth medium is used to encapsulate *Lactobacillus* then this may be entirely or within an encapsulation matrix formed of the growth medium and/or another material.

In some embodiments, the *Lactobacillus* of the synbiotic composition is concentrated and/or freeze dried.

The synbiotic composition may be in the form of one or more capsules or tablets. If the composition is in the form of two capsules or tablets, the probiotic component may be contained within a first capsule or tablet and the prebiotic growth medium is contained within a second capsule or tablet. These capsules may be taken at the same or different time intervals.

The synbiotic composition may be in the form of a drinkable liquid and/or ingestible powder format and/or can be mixed with a solid or liquid food stuff. If the composition is in the form of a drinkable liquid and/or powder format and/or can be mixed with a solid or liquid food stuff and wherein the probiotic component is formulated separately and may be delivered separately from the prebiotic growth medium.

The compositions may be for use as a dietary supplement. The dietary supplement may be for improving gut health and/or the microbial flora of an individual.

The compositions may for use in increasing the population of *Lactobacillus* in the gut of an individual. The population may at least partially be an or the indigenous population of the individual.

In a further aspect of the present invention, there is provided method of producing a synbiotic composition comprising the steps:
(a) providing a probiotic component comprising one or more strains of *Lactobacillus* spp.;
(b) providing a prebiotic component comprising a growth medium which comprises one or more components selected from: xylooligosaccharides, cellobiose and/or gentiooligosaccharides; and
(c) combining the one or more strains of *Lactobacillus* spp. with a quantity of the growth medium so as to form an effective dose of the composition.

The one or more strains of *Lactobacillus* spp. may comprise one or more strains of *L. rhamnosus* and/or one or more strains of *L. plantarum*. The one or more strains of *L. rhamnosus* may comprise *L. rhamnosus* GG and/or *L. rhamnosus* ATCC 53103 and the one or more strains of *L. plantarum* may comprise *Lactobacillus plantarum* 2830 (ECGC 13110402).

Preferably, the method is used to produce a prebiotic composition or a synbiotic composition as herein above described.

DETAILED DESCRIPTION OF THE INVENTION

Embodiments of the present invention will now be described, by way of example only and with reference to the following Figures:

FIG. 1 shows a graph of pure culture screening of *L. rhamnosus* ATCC 53103 on commercially available oligo/polysaccharides in MRS modified growth media whereby the glucose content has been substituted with 1% (w/v) test oligo/polysaccharide (MRS+Glu+LR; Inulin (Raftiline HP); Orafti P95 (Raftilose); Orafti ST (Raftiline ST); Short FOS (Actilight); and Wheat Arabinoxylan (Low Viscosity);

FIG. 2 shows a graph of pure culture screening of *L. rhamnosus* ATCC 53103 on commercially available oligo/polysaccharides (Resistant Dextrin (Nutriose); Lactulose-sucrose; Glucosyl-lactose; Lactosyl-fructoside; and GOS synthesized from lactulose DP3);

FIG. 3 shows a graph of pure culture screening of *L. rhamnosus* ATCC 53103 on commercially available oligo/polysaccharides (Inulin (Raftiline); Orafti P95 (Raftilose); Orafti ST (Raftiline ST); Short FOS (Actilight); Wheat Arabinoxylan (Low Viscosity); Wheat Arabinoxylan (Medium Viscosity); Alpha-glucooligosaccharides (Bio-ecolians); Gentiooligosaccharides; Levan; Fibersol C*Actistar (Resistant Starch);

FIG. 4 shows a graph of pure culture screening of *L. rhamnosus* ATCC 53103 on commercially available oligo/polysaccharides (Nutriose (Resistant Dextrin); Lactulose-sucrose; Glucosyl-lactose; Lactosyl-fructoside; Lactulose; Sunfiber (Glucomannan); alphaGOS from Olygose; and FOS from finefoods);

Figure 1:
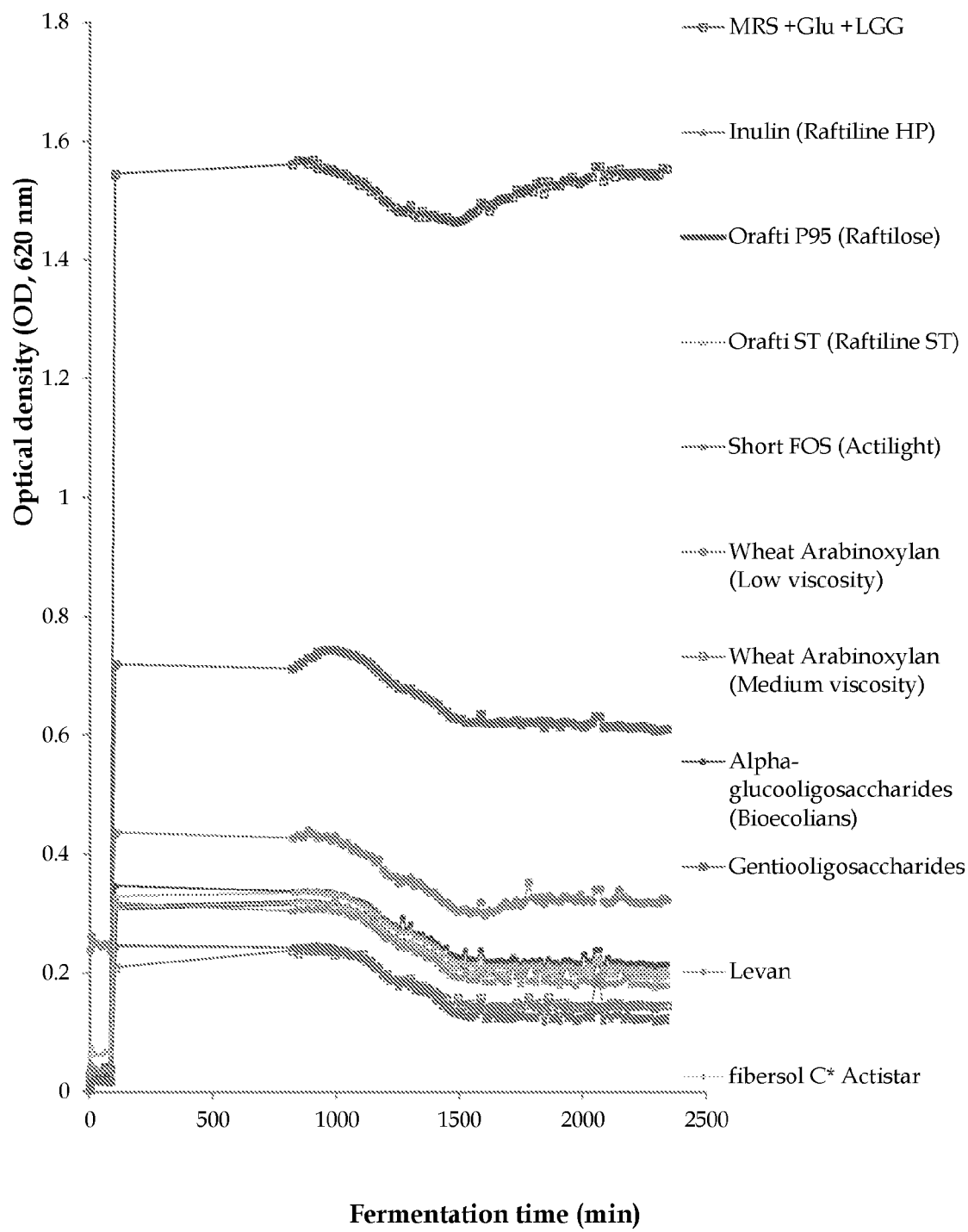
Figure 2:
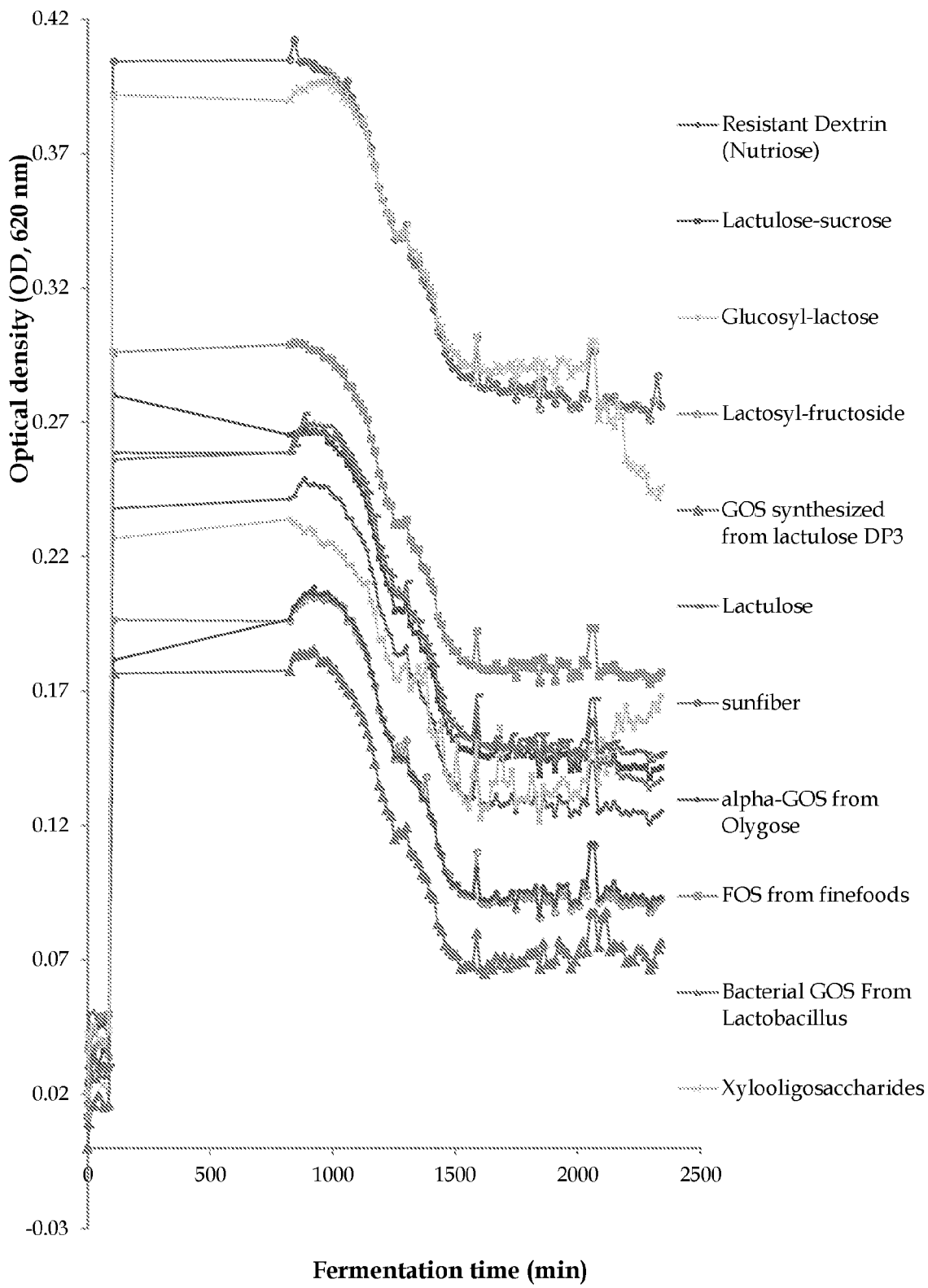
Figure 3:
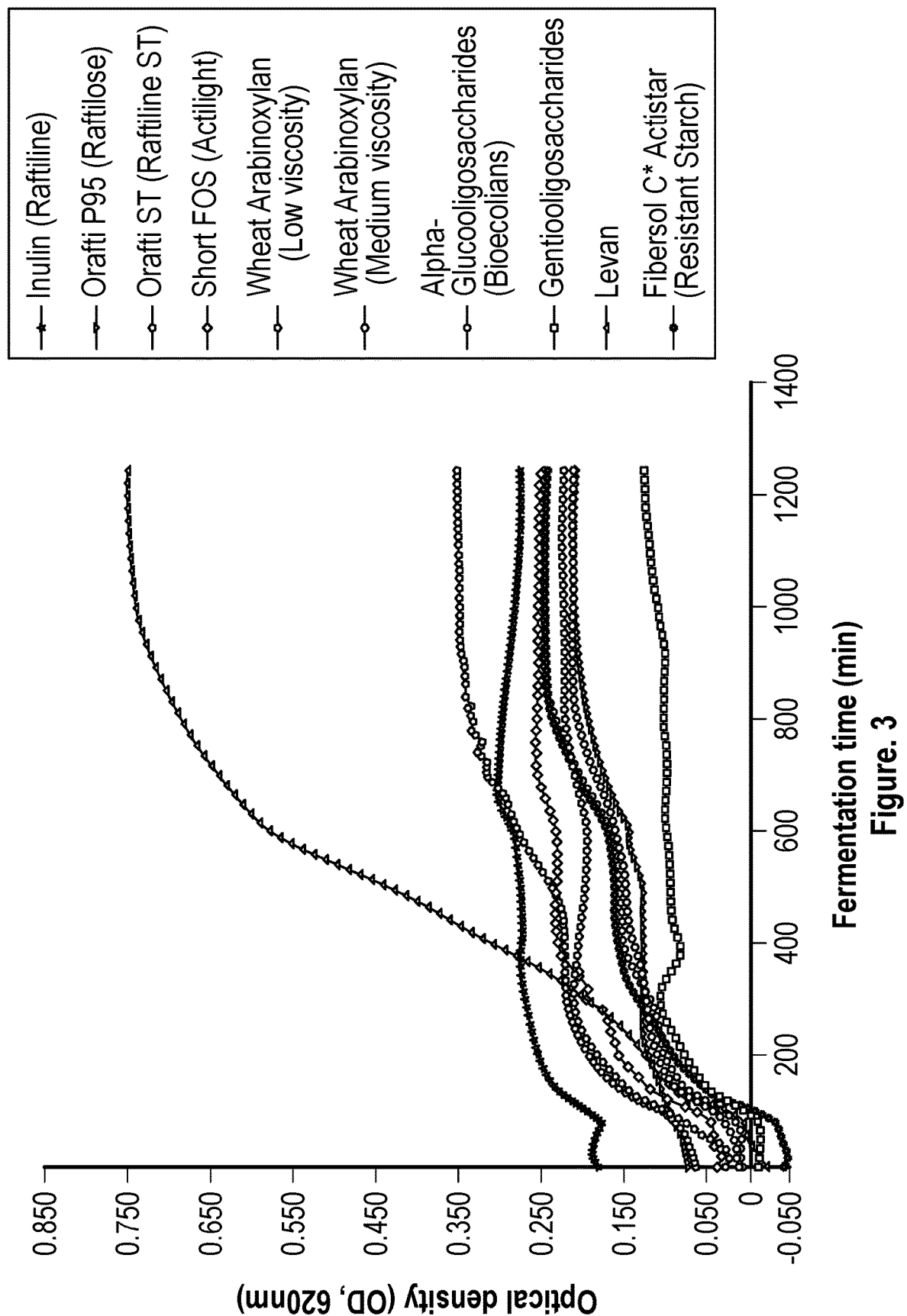
Figure 4:
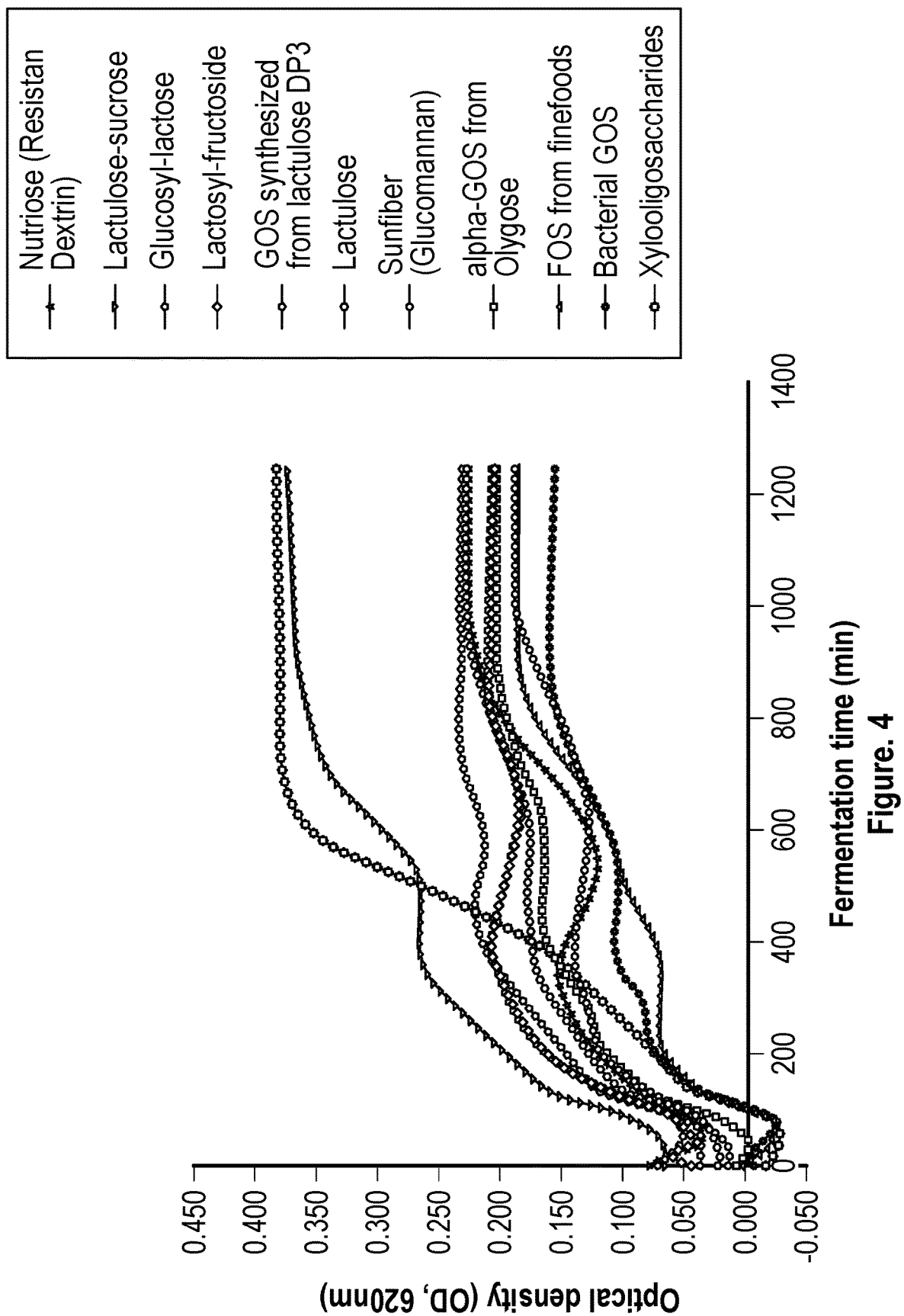
Figure 5A:
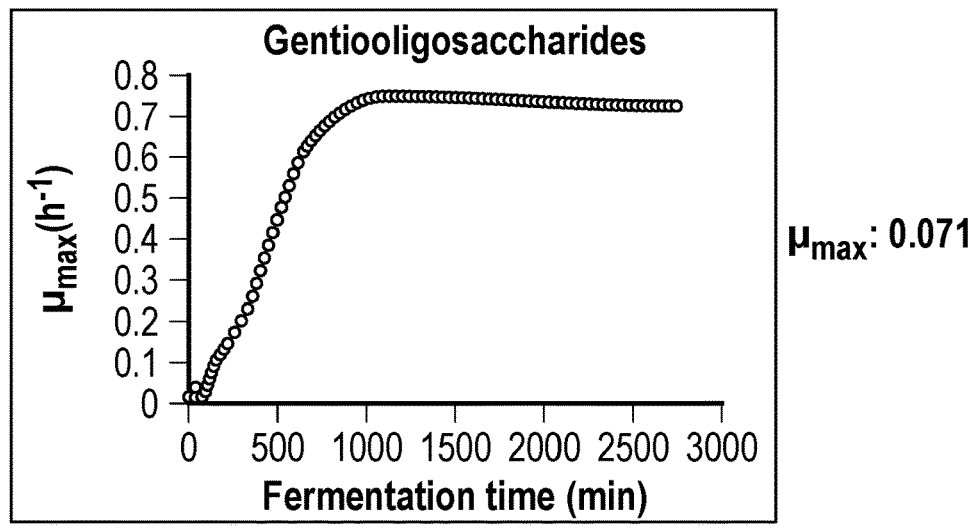
FIG. 5A-5C are graphs showing the pure culture growth rates of *L. rhamnosus* ATCC 53103 on (A) Gentiooligosaccharides; (B) Galactomannan (Sunfiber); and (C) Xylooligosaccharides.
Figure 5B:
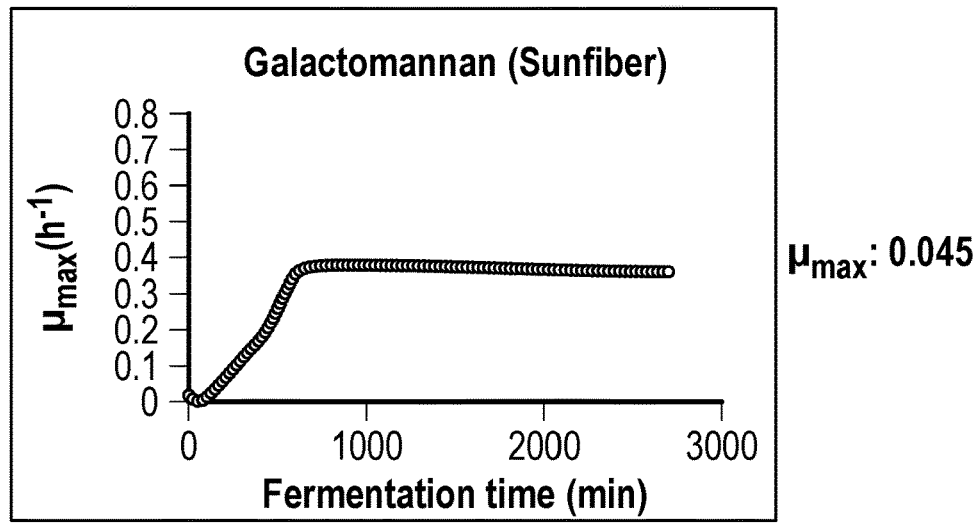
Figure 5C:
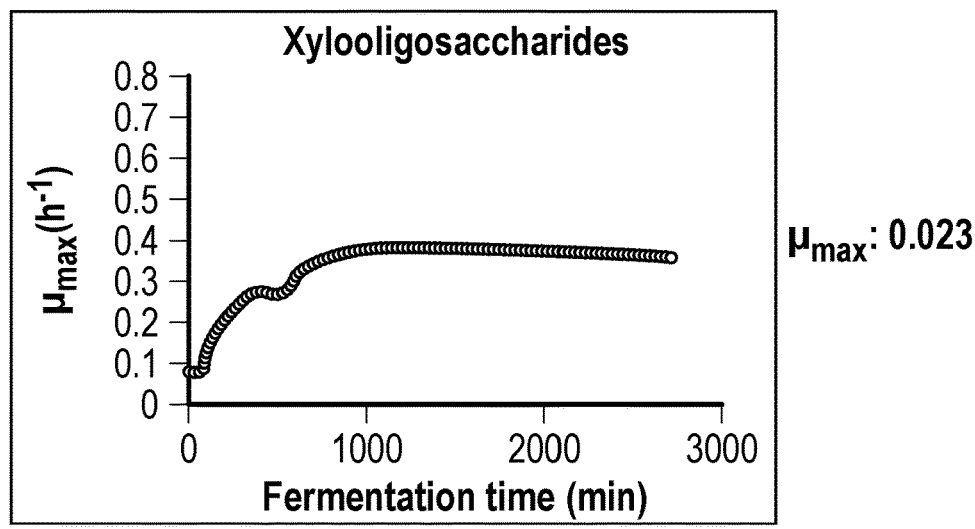
Figure 6:
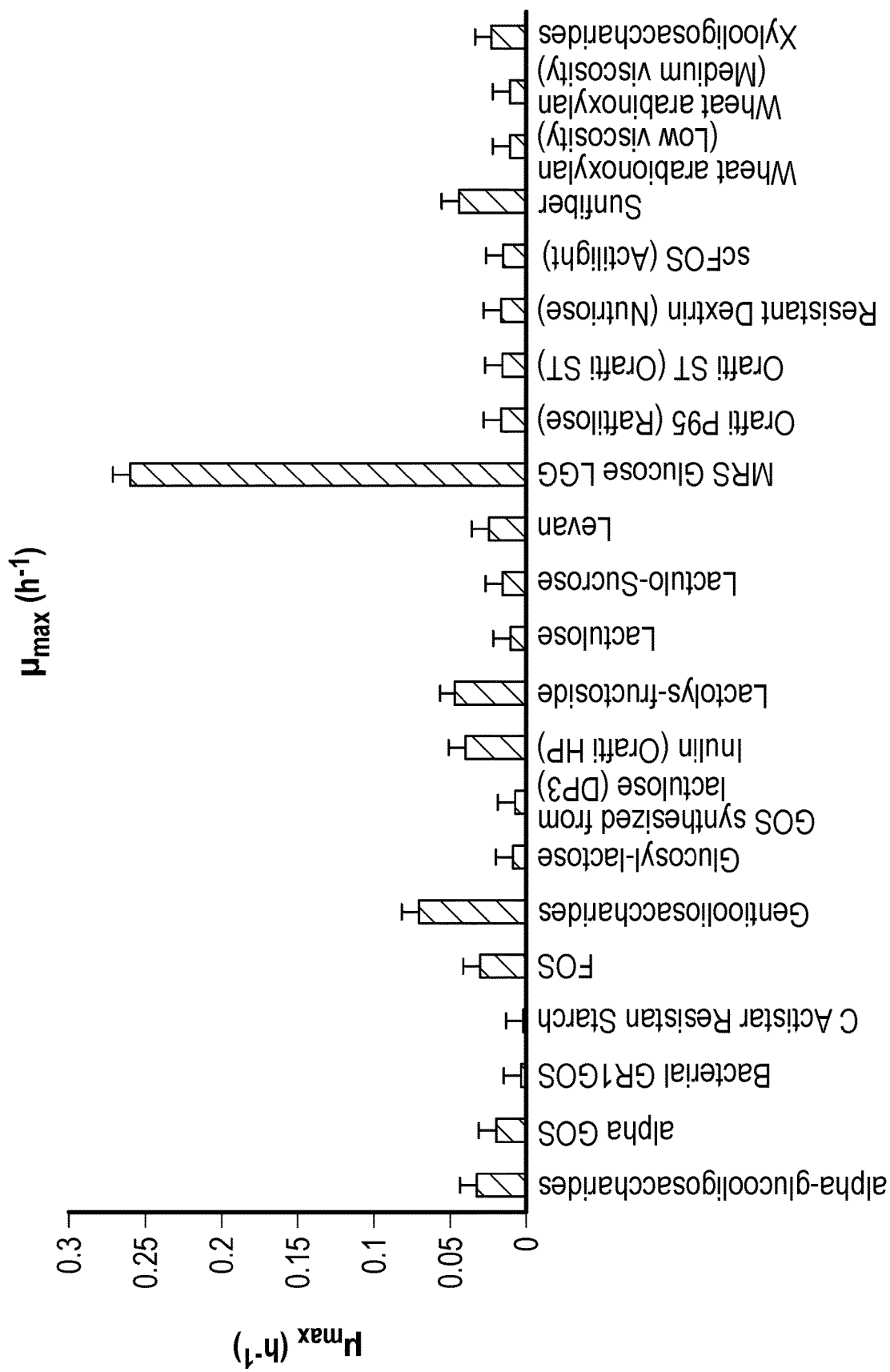
FIG. 6 is a graph showing growth rates ($\mu_{max}(h^{-1})$) for *L. rhamnosus* ATCC 53103 on a range of commercially available oligo/polysaccharides.
Figure 7:
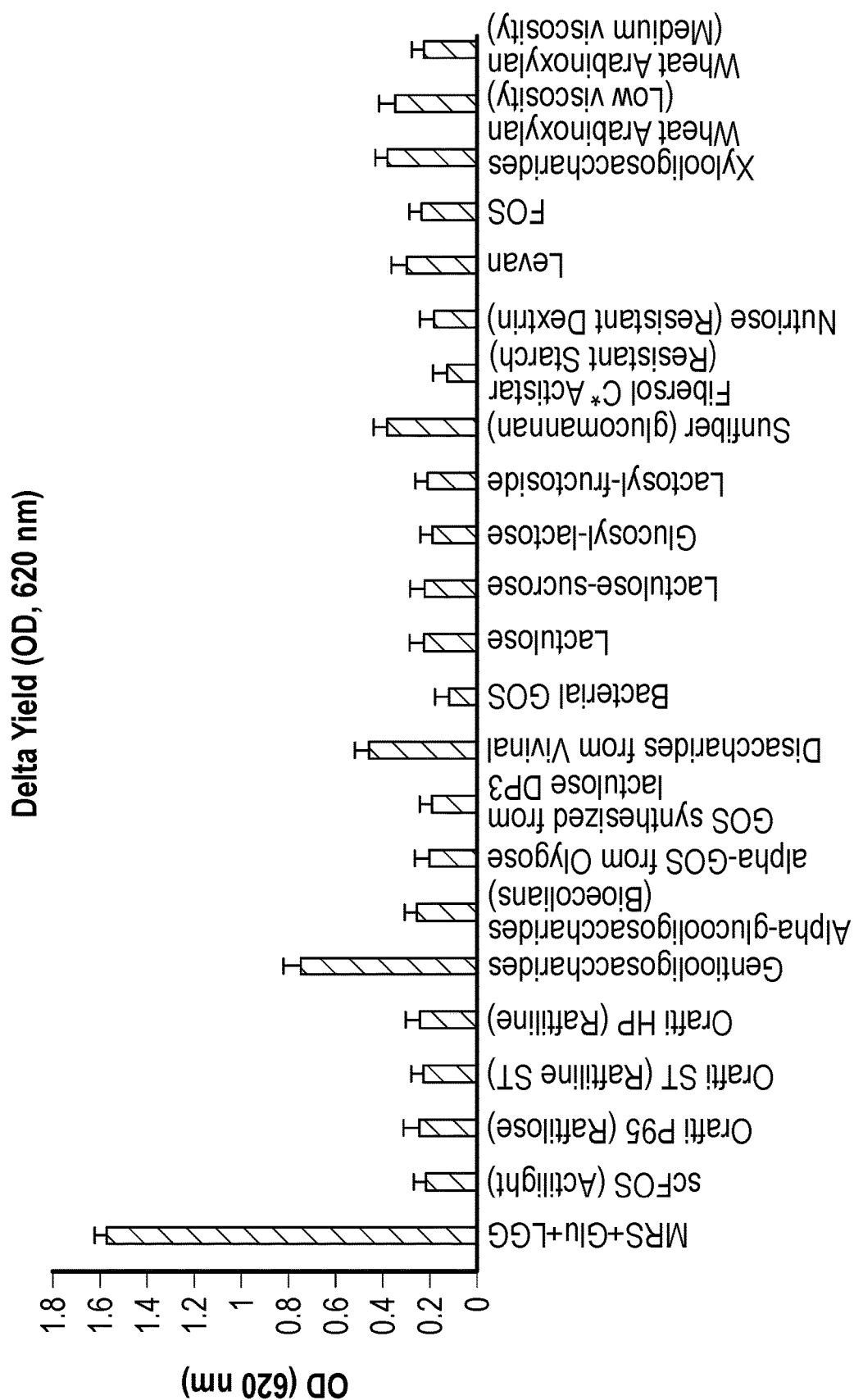
FIG. 7 is a graph showing Delta Yield (OD, 620 nm) for *L. rhamnosus* ATCC 53103 on a range of commercially available oligo/polysaccharides.
Figure 8:
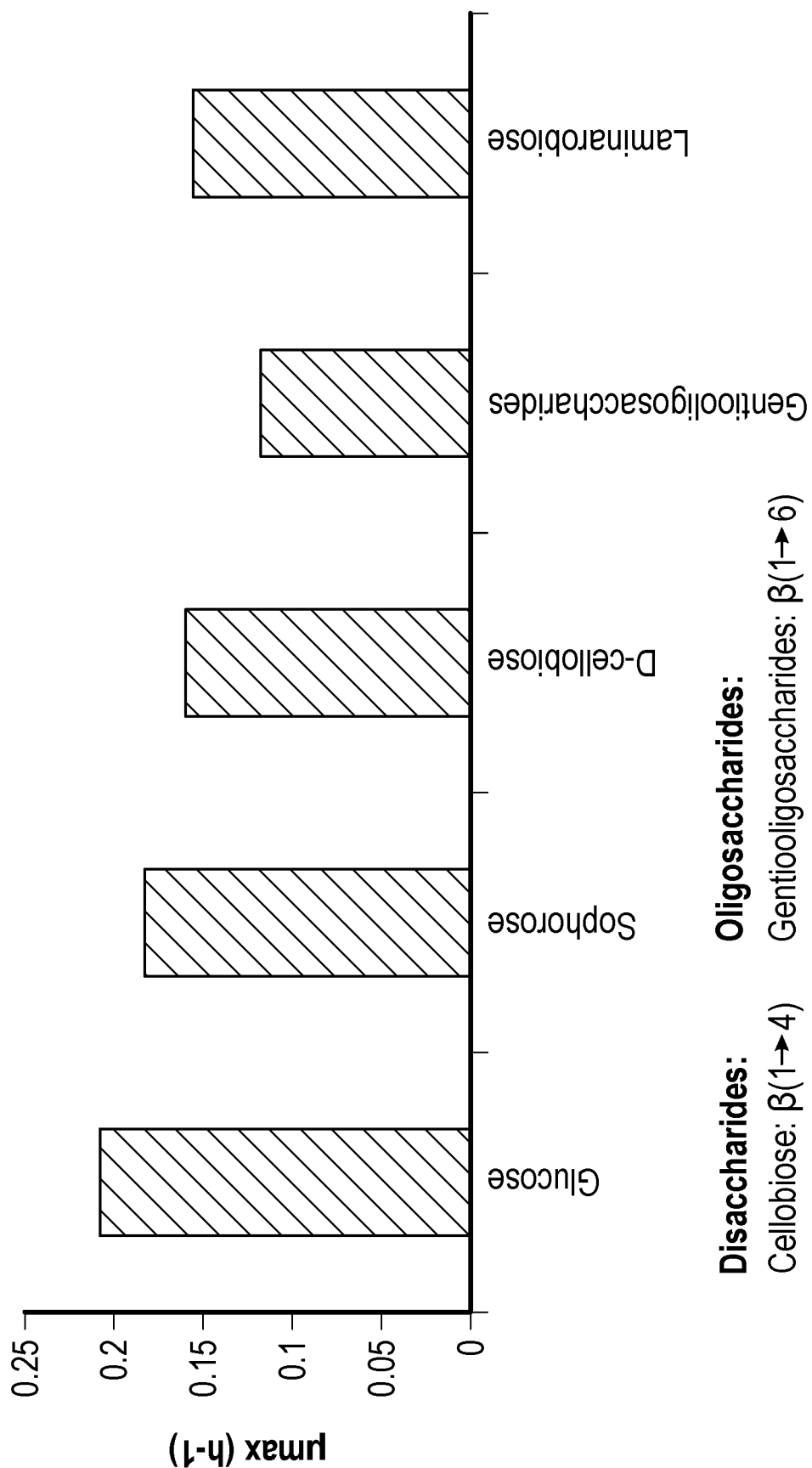
Figure 9:
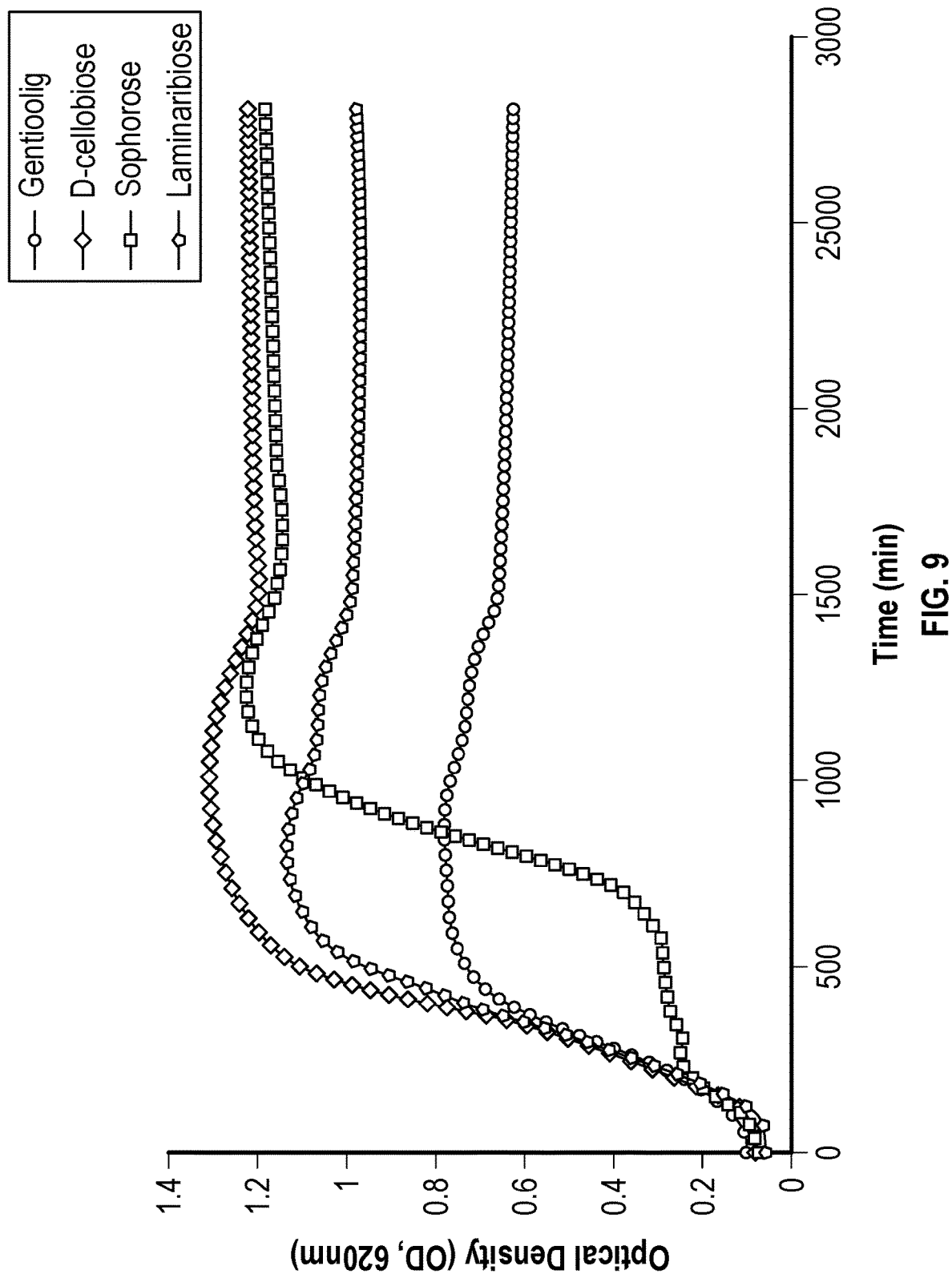
Figure 10:
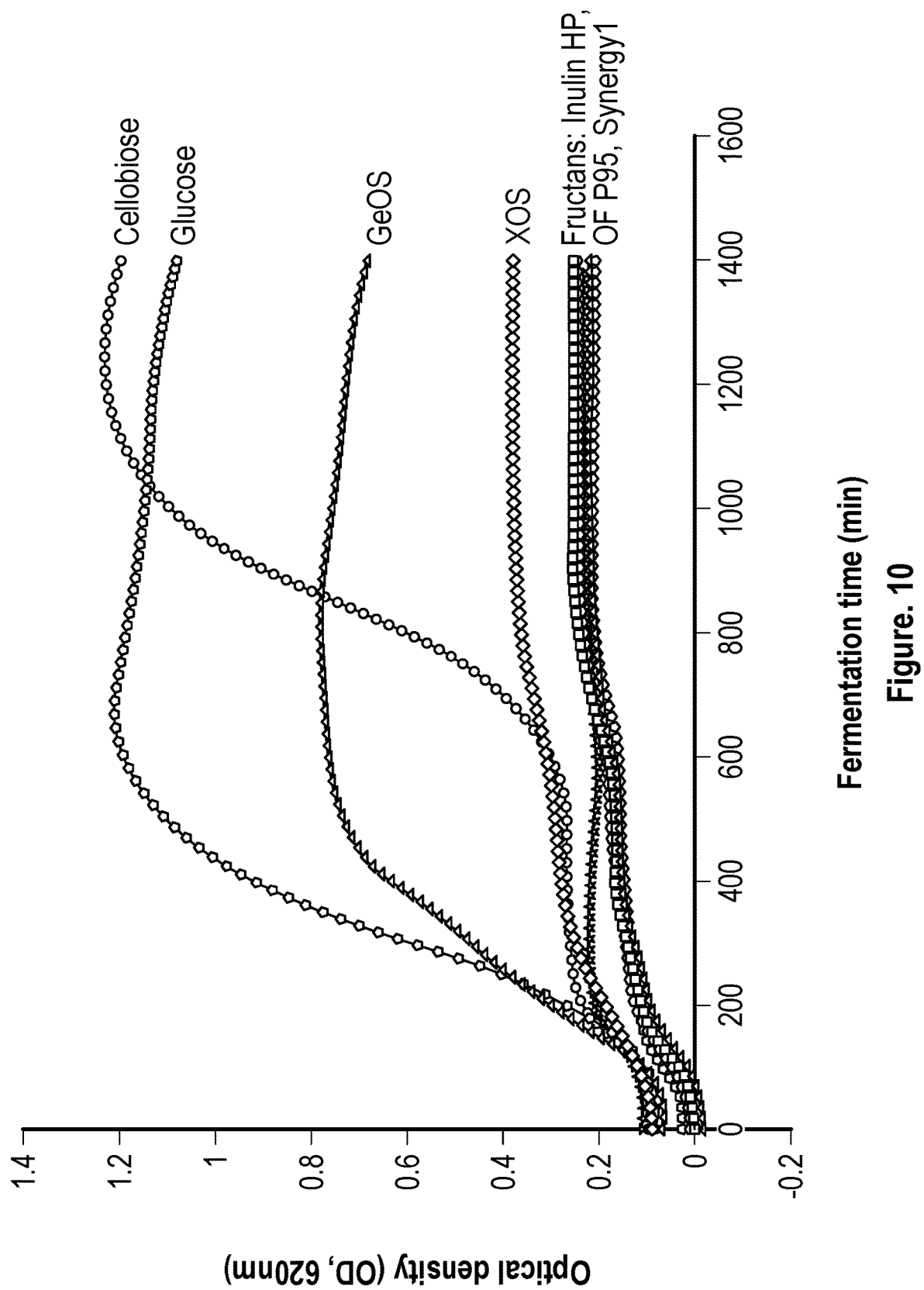
Figure 11A:
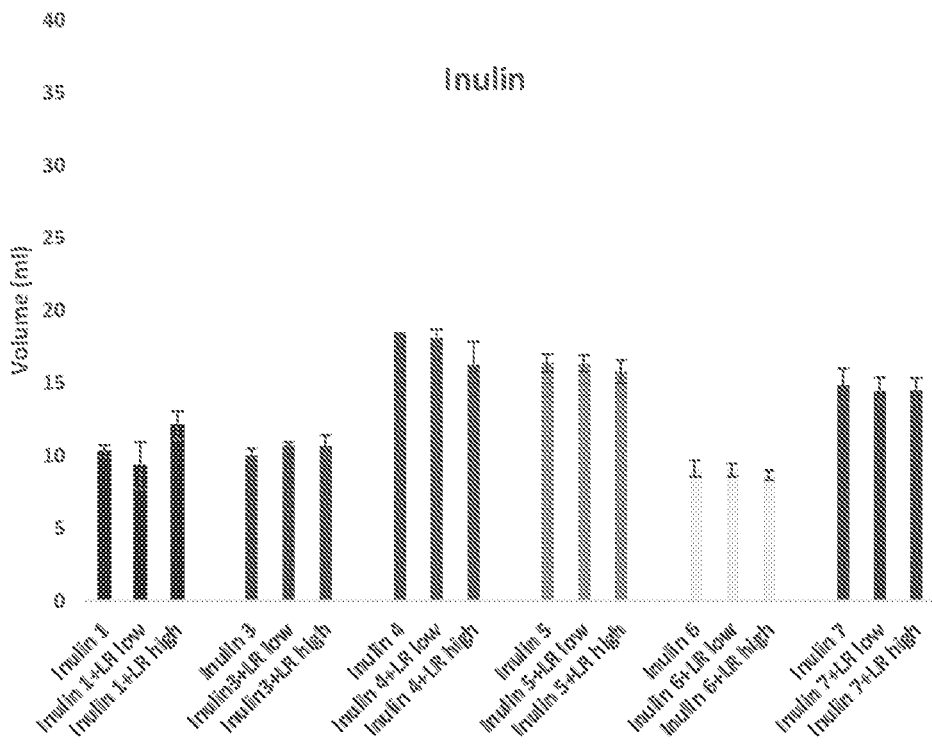
Figure 11B:
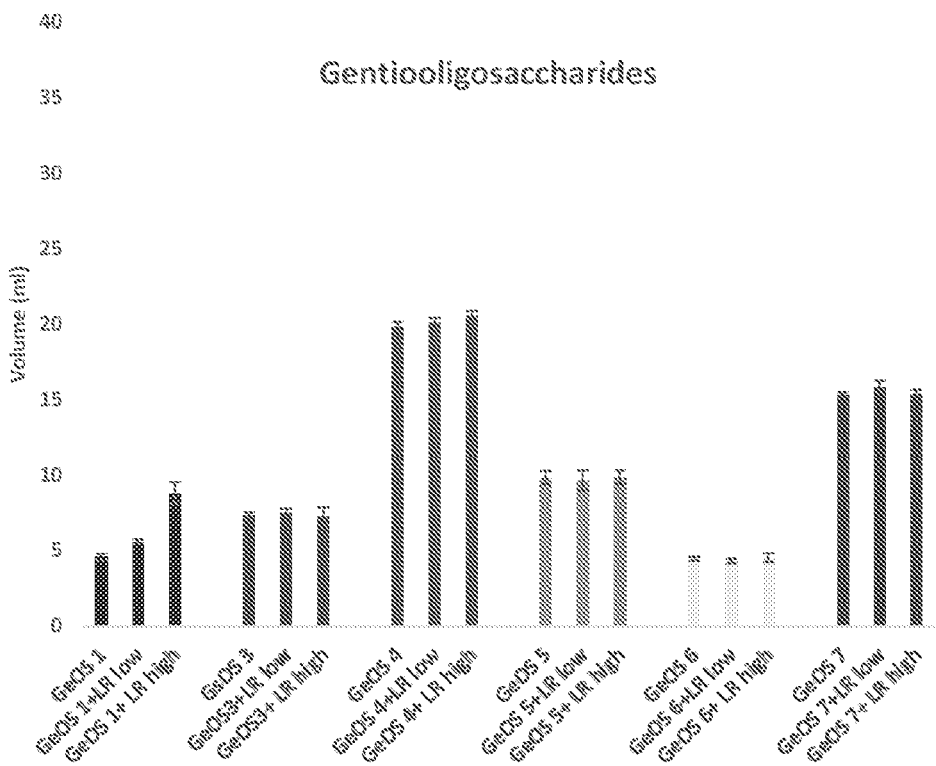
Figure 11C:
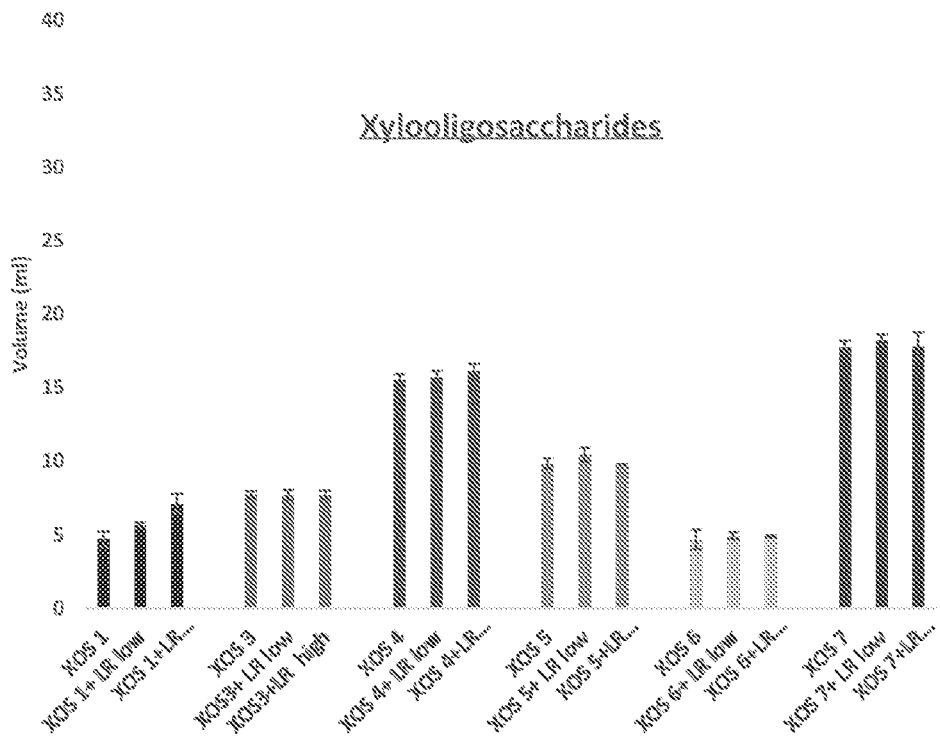
Figure 11D:
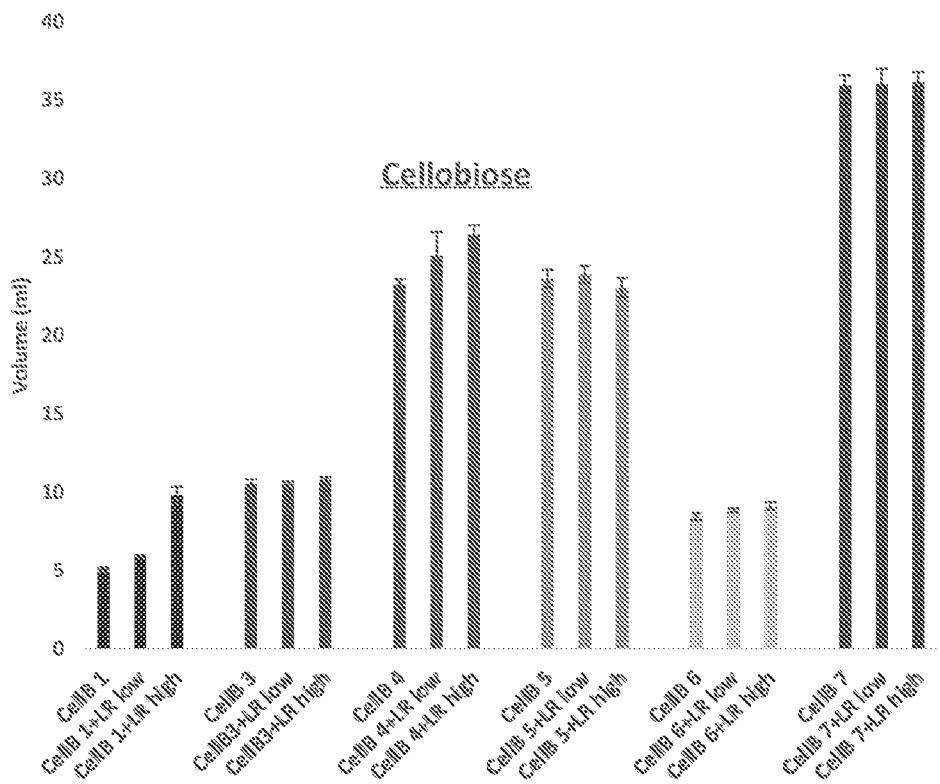
Figure 12A:
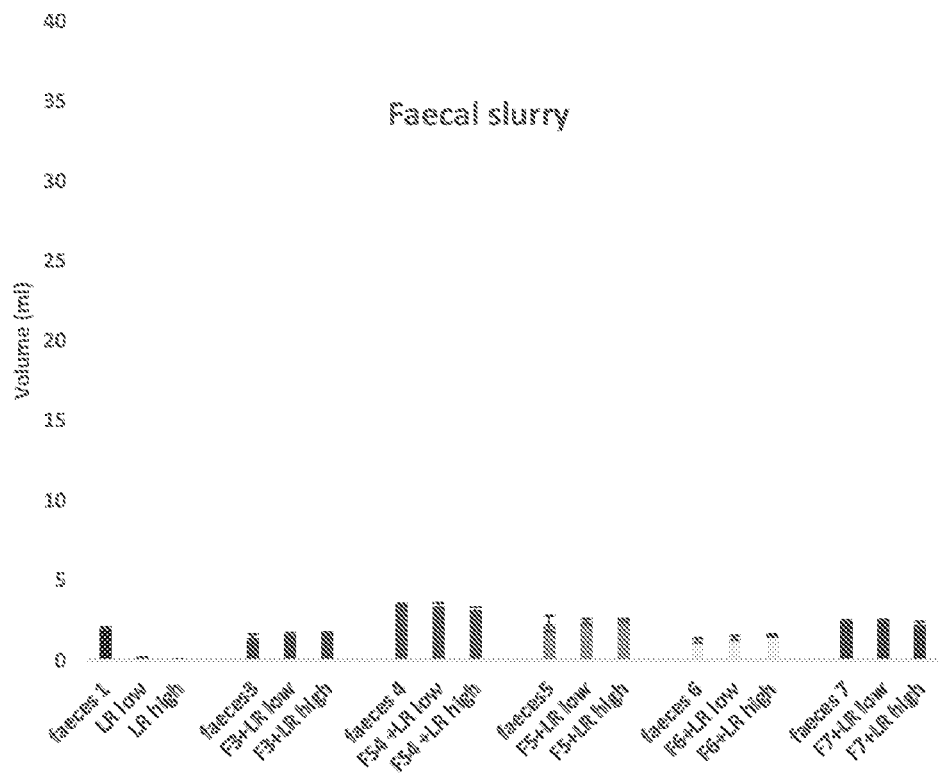
Figure 12B:
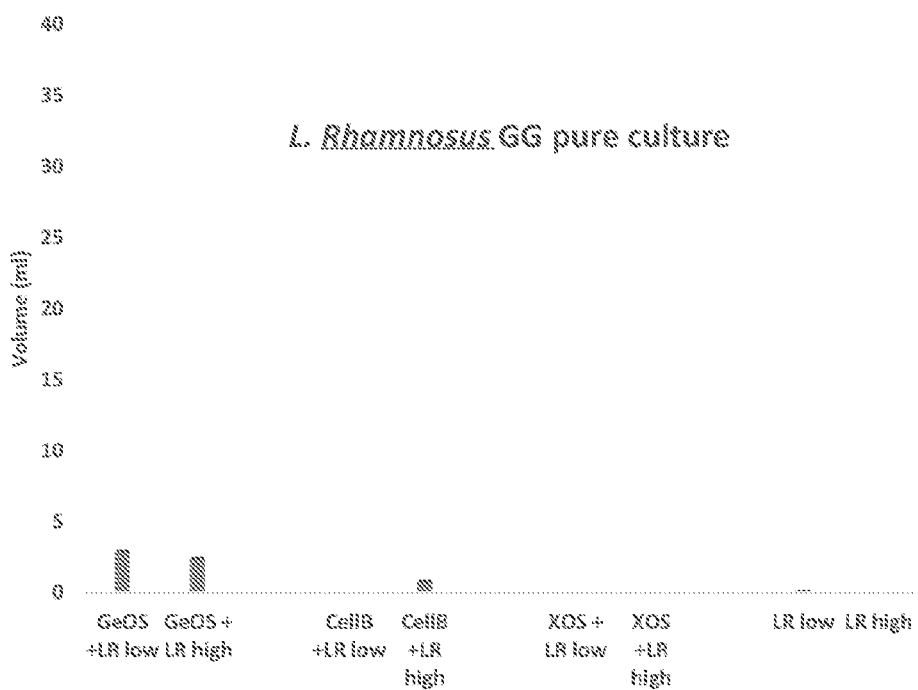
Figure 13:
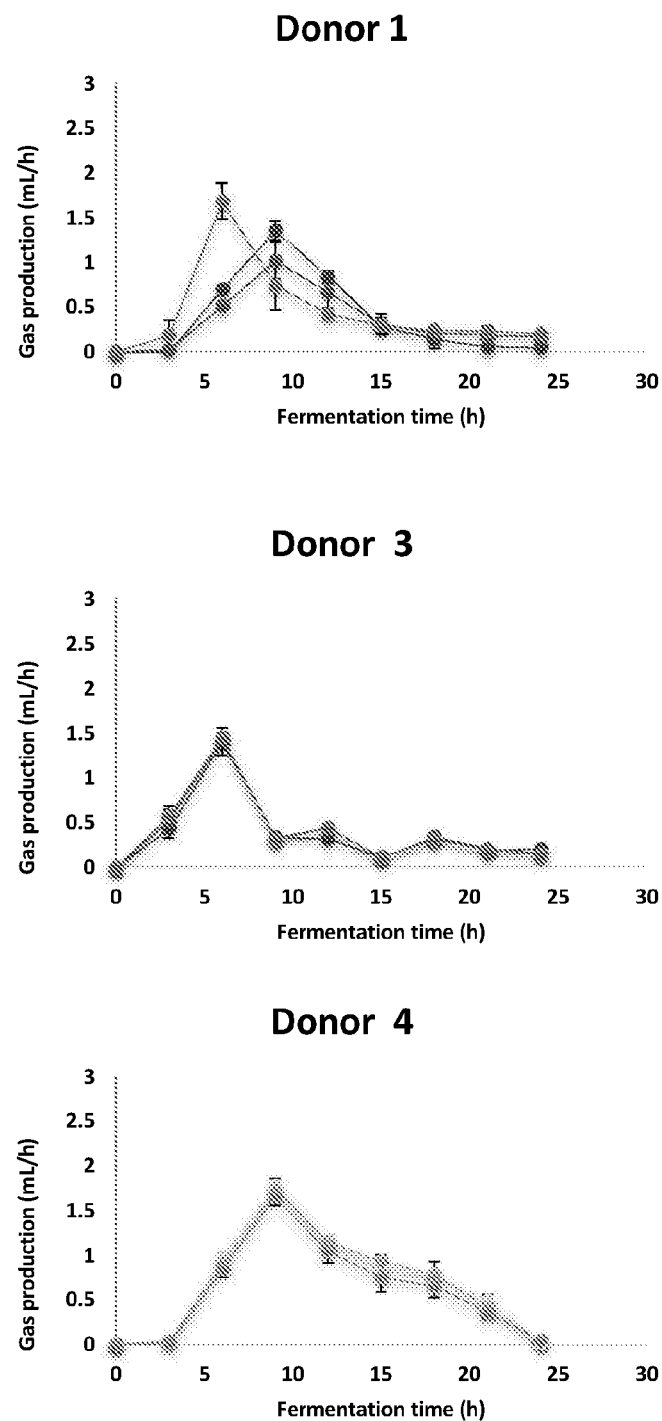
Figure 15:
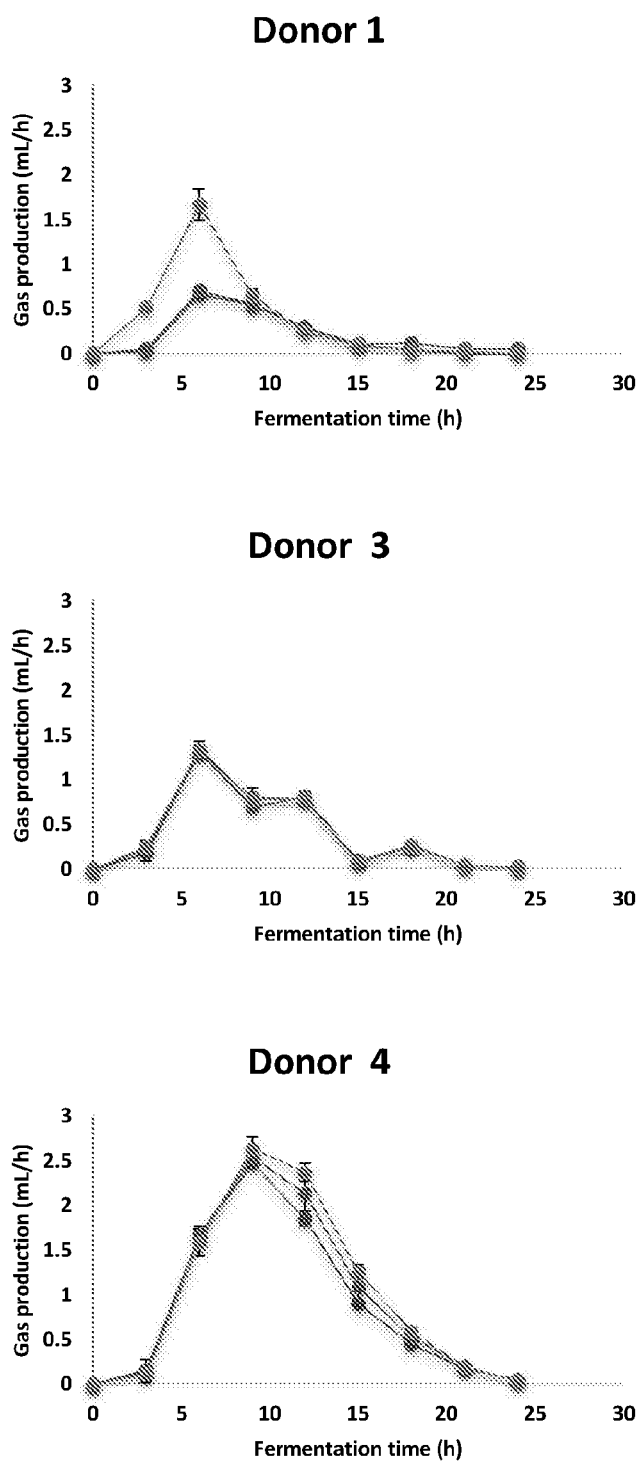
Figure 17:
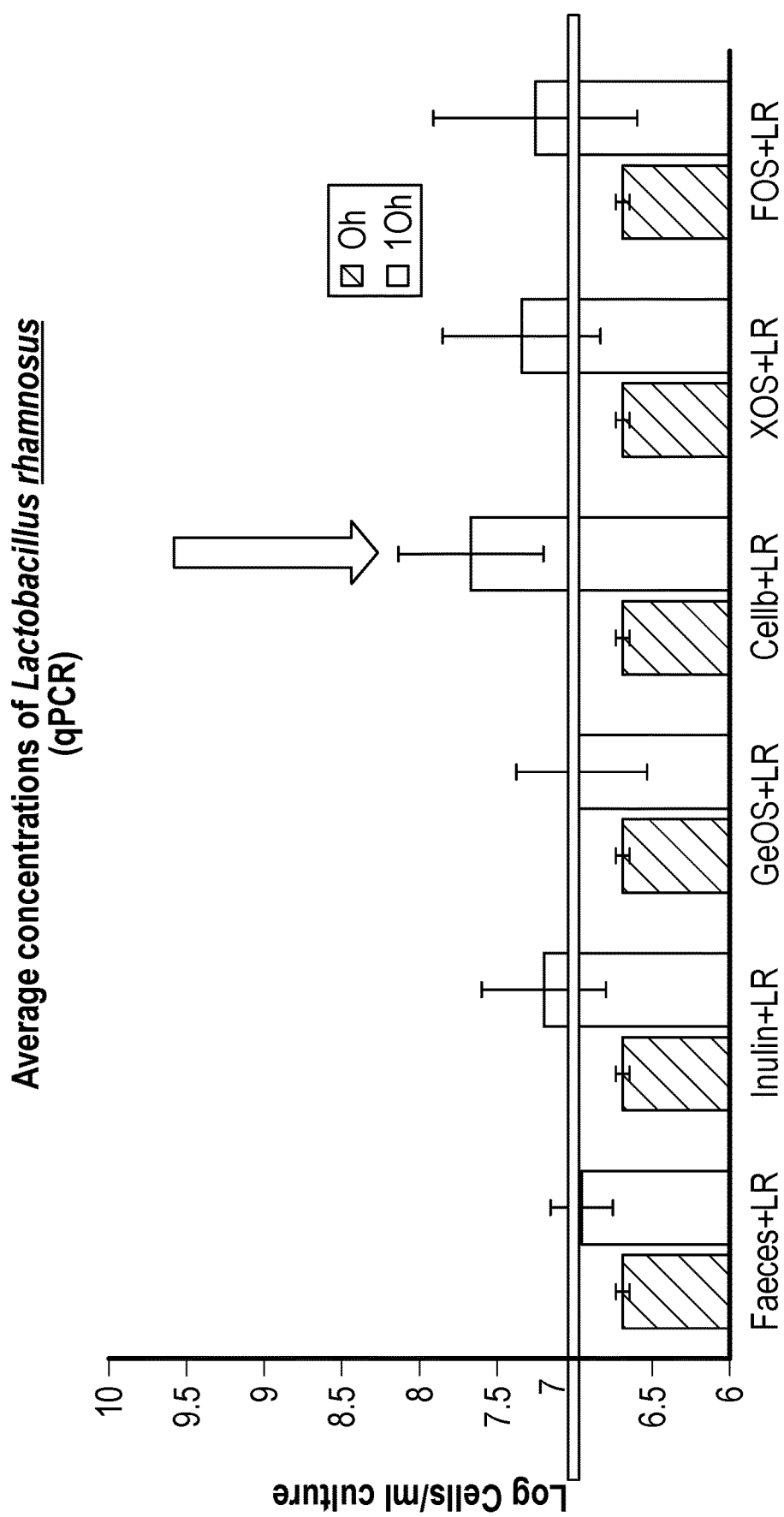
Figure 18:
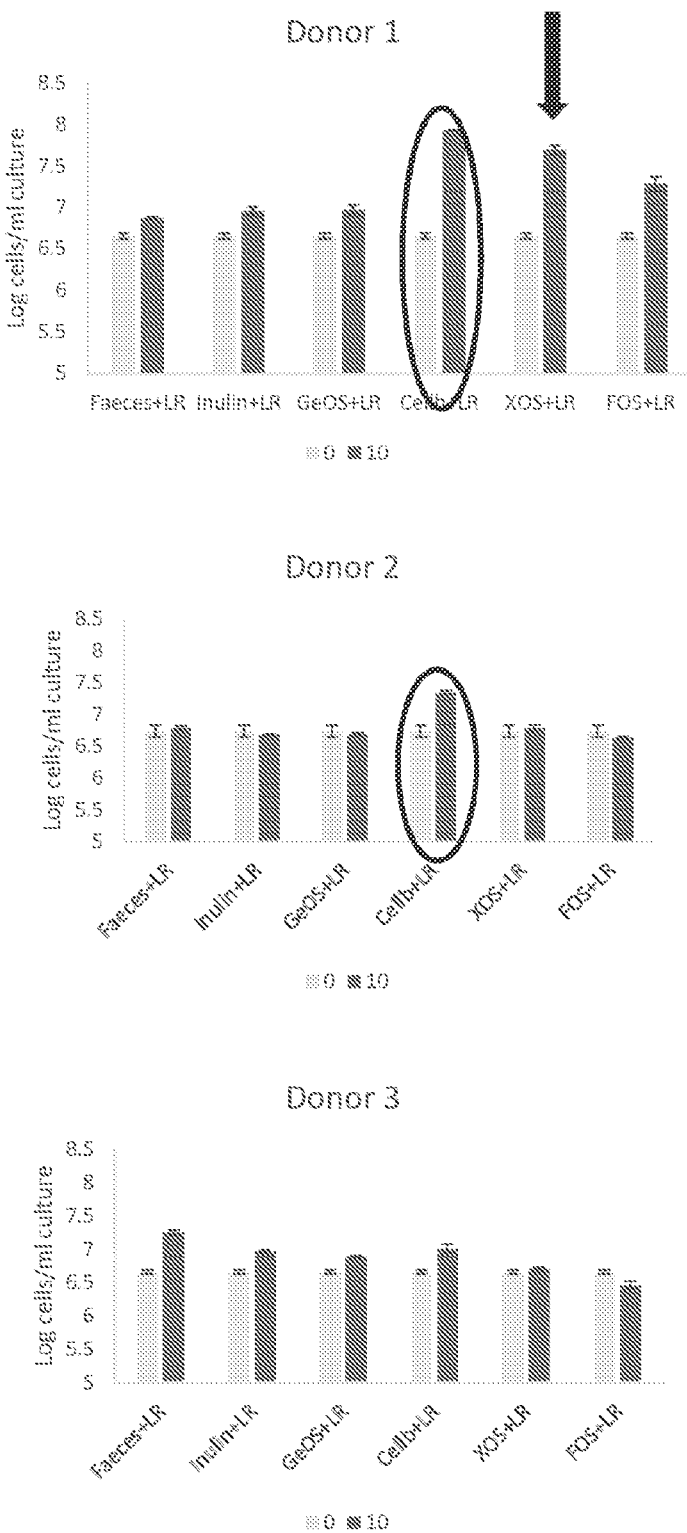
Figure 18:
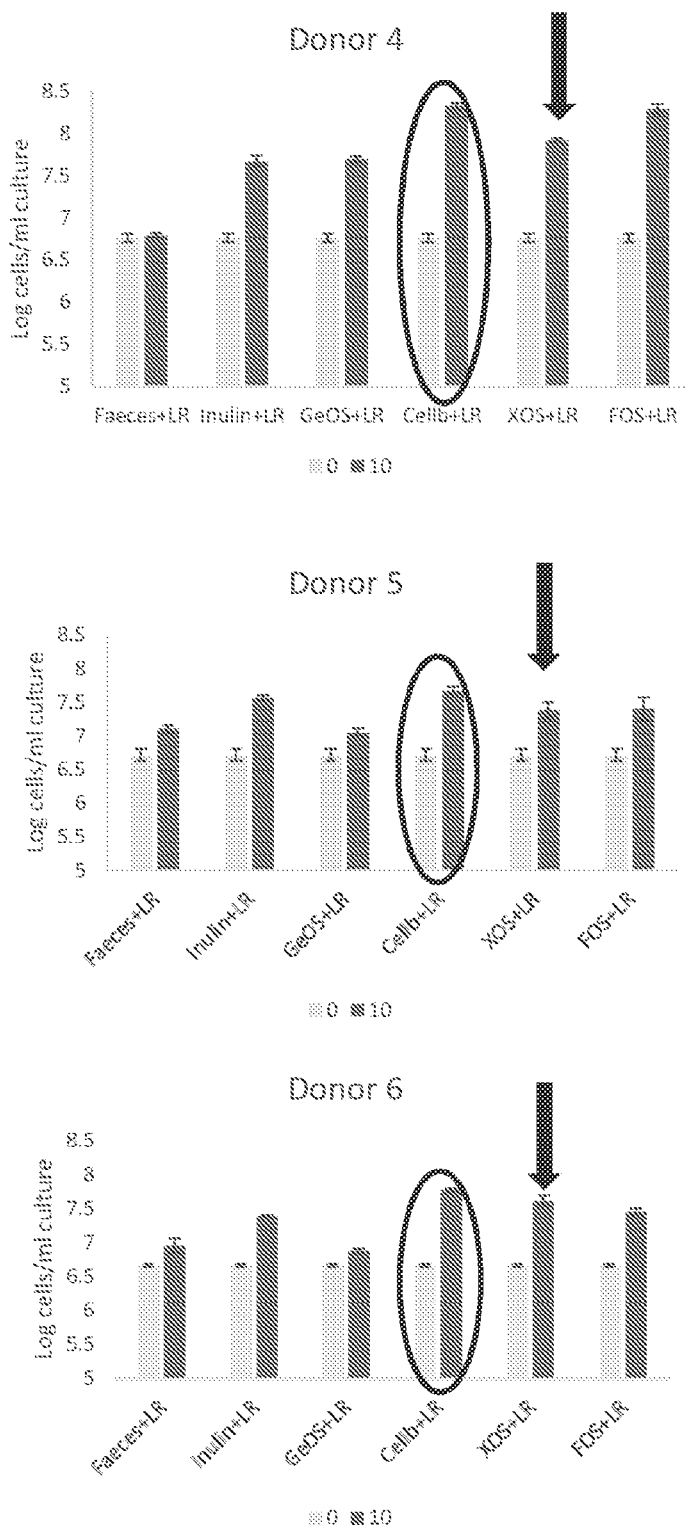
Figure 19:
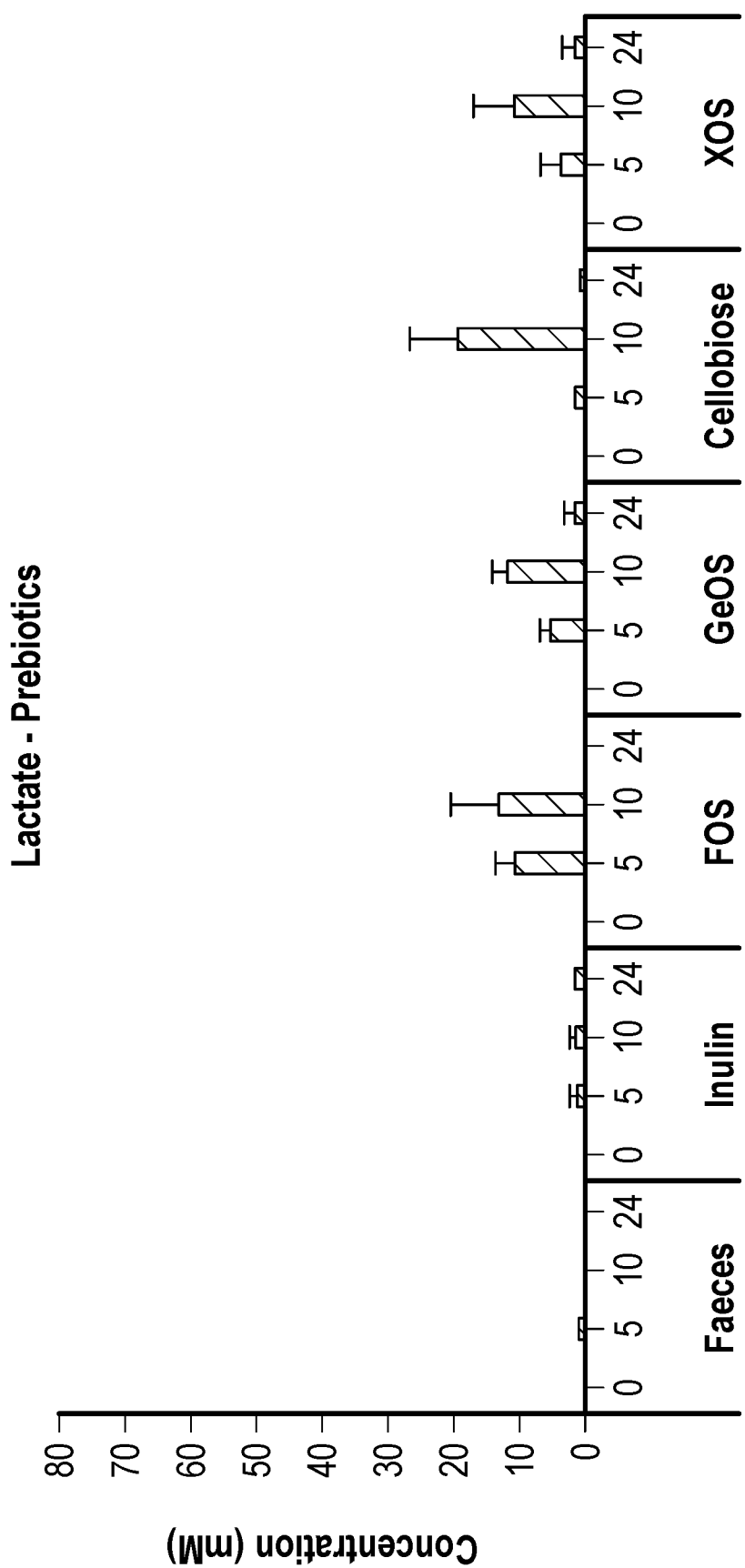
Figure 19:
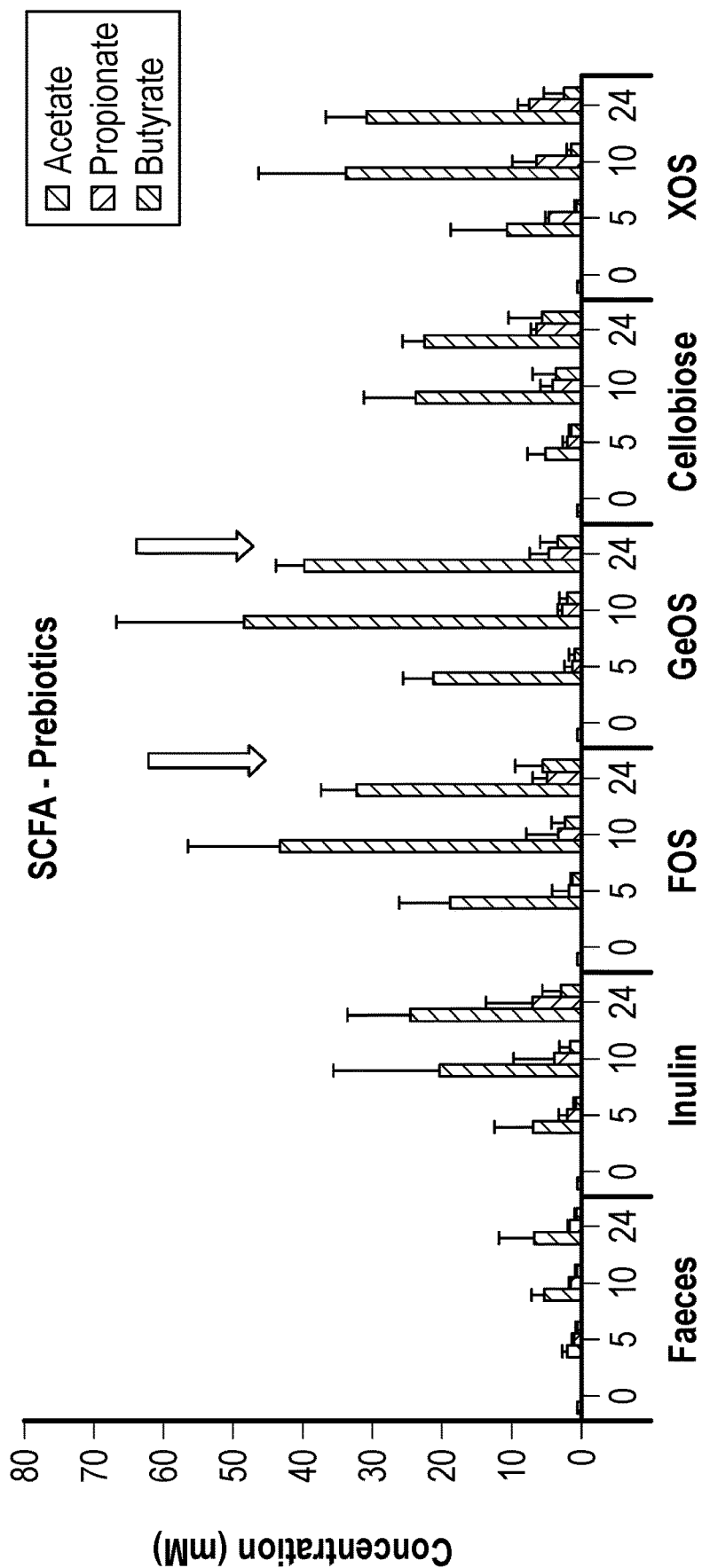
Figure 19:
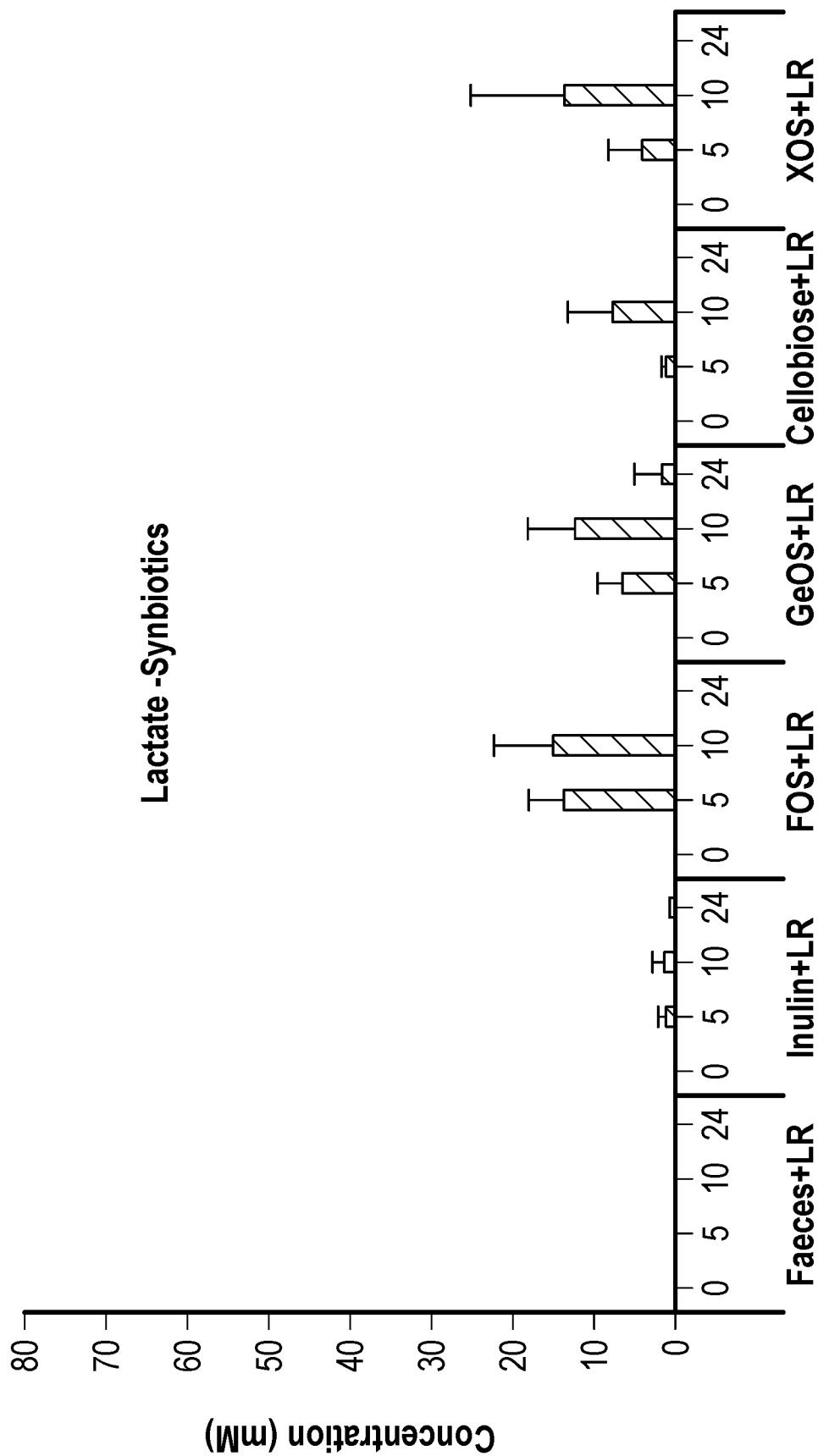
Figure 19:
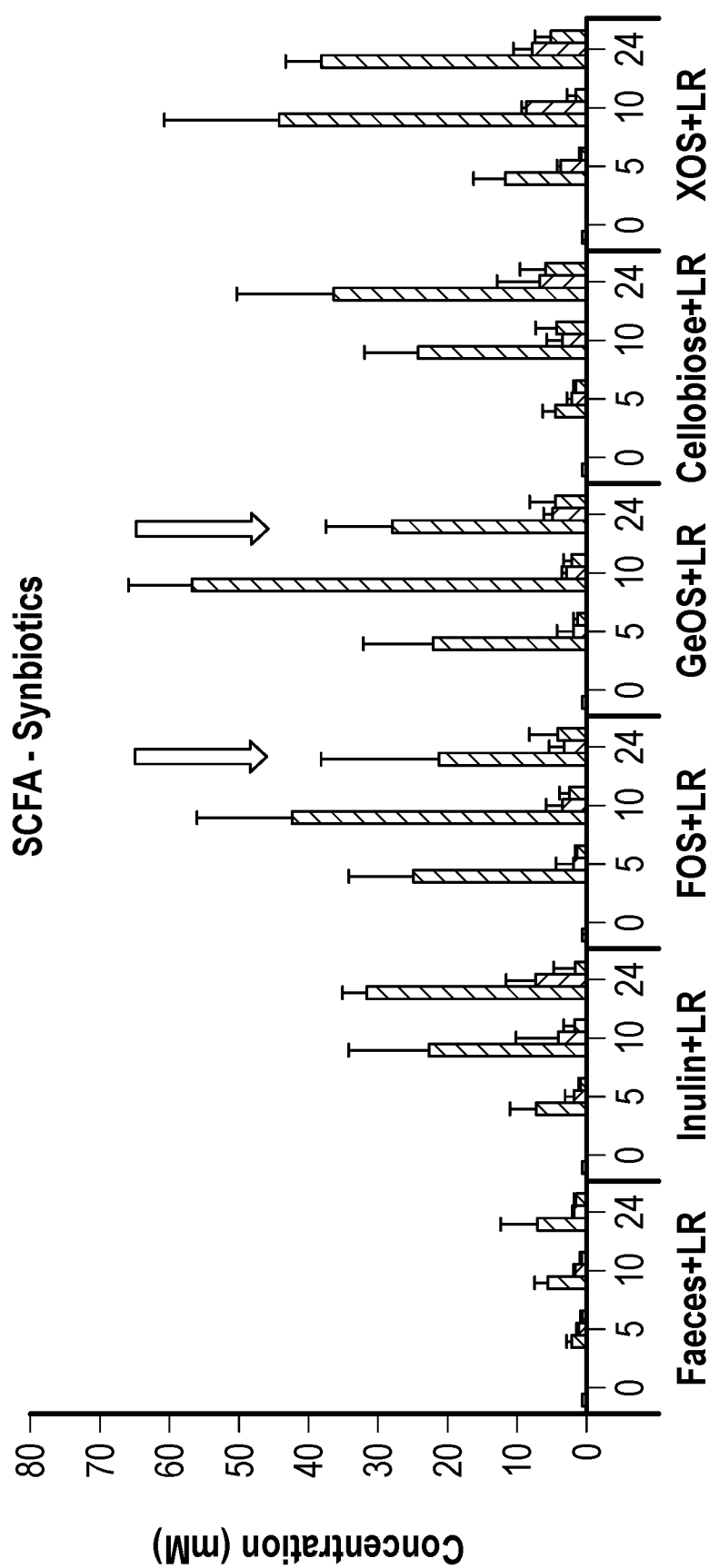
Figure 20:
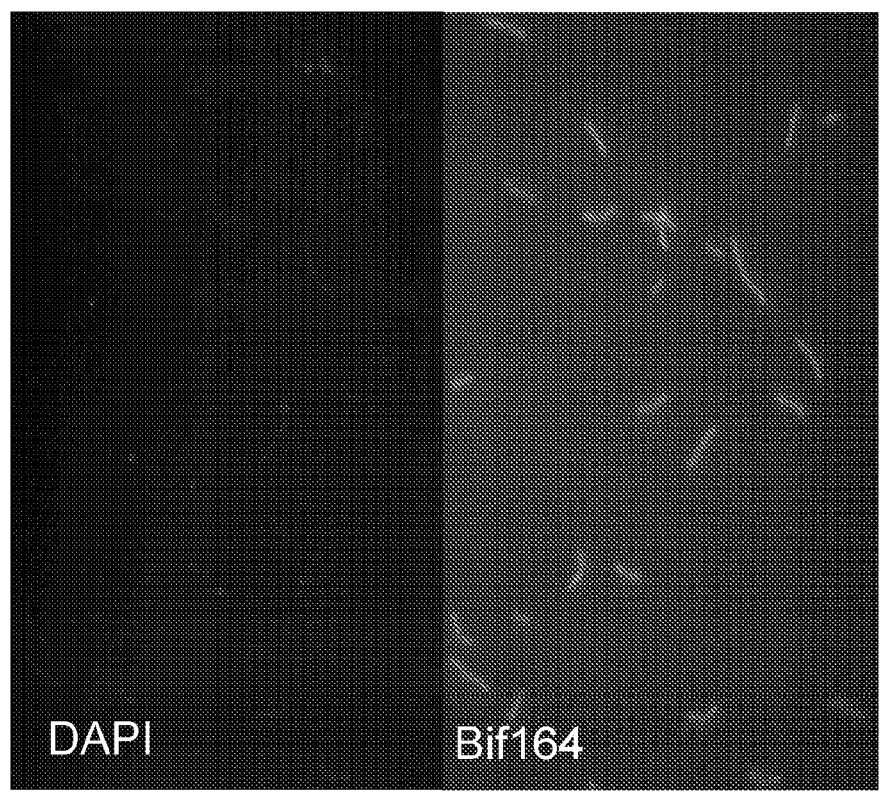
Figure 21:
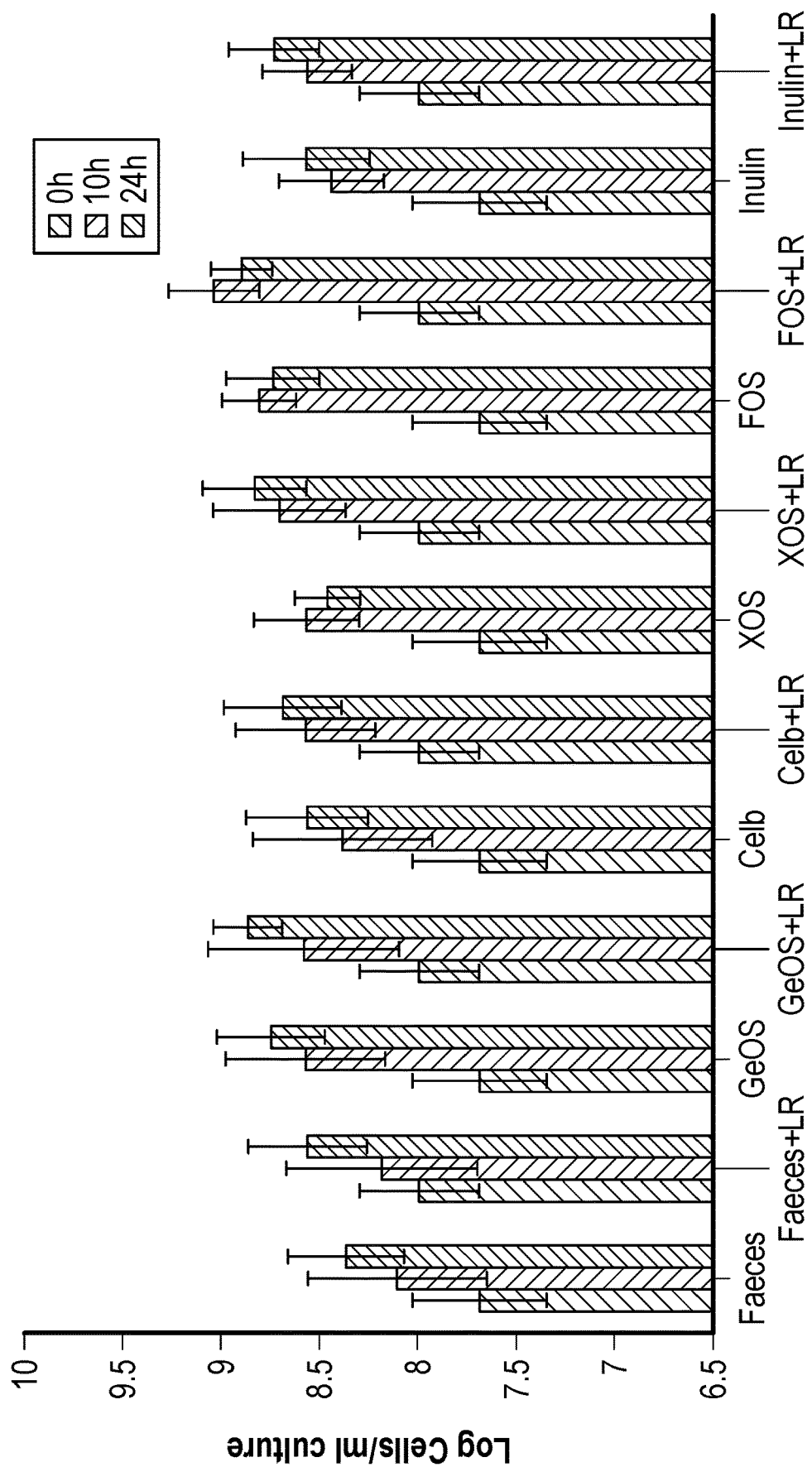
Figure 22:
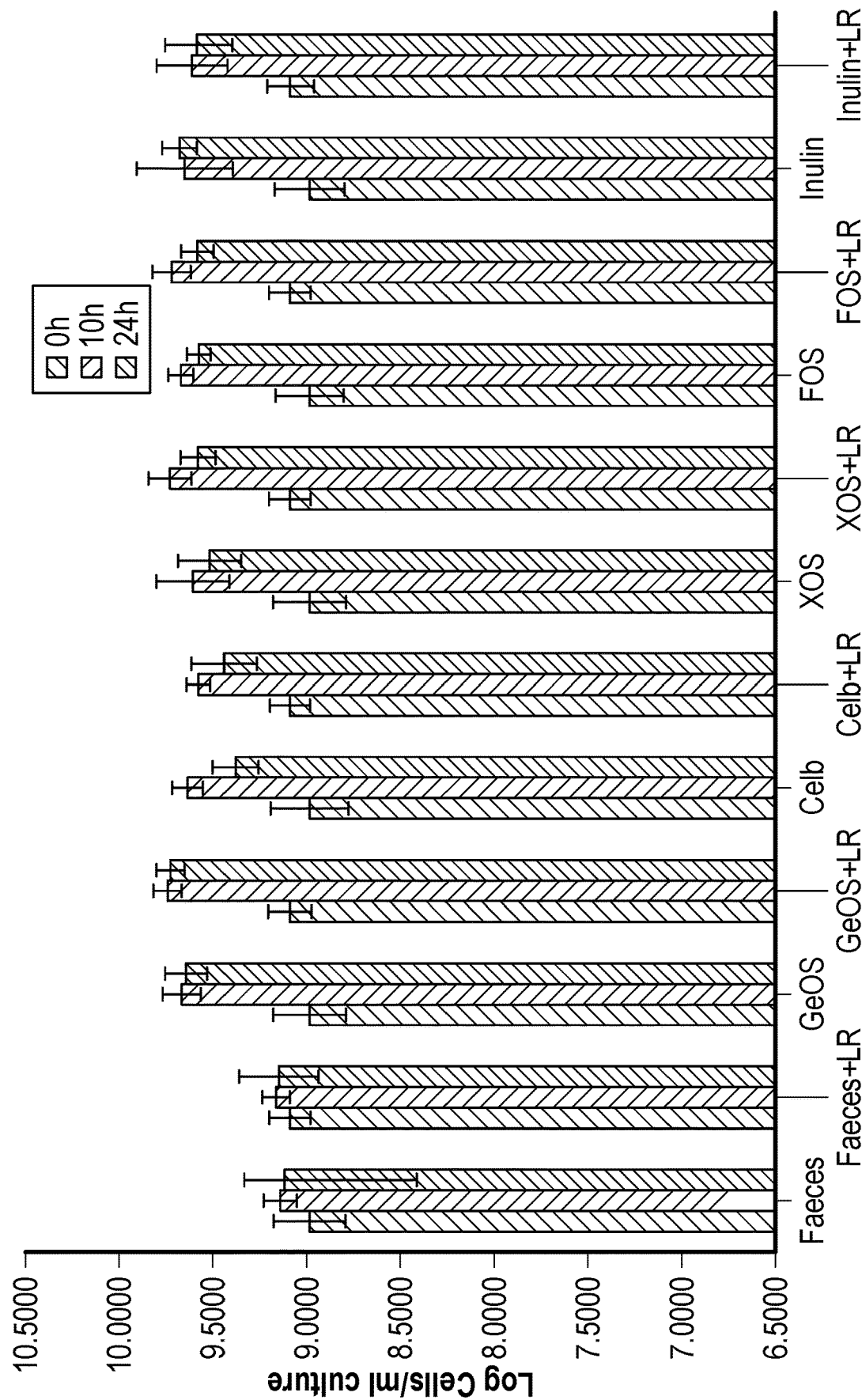
Figure 23:
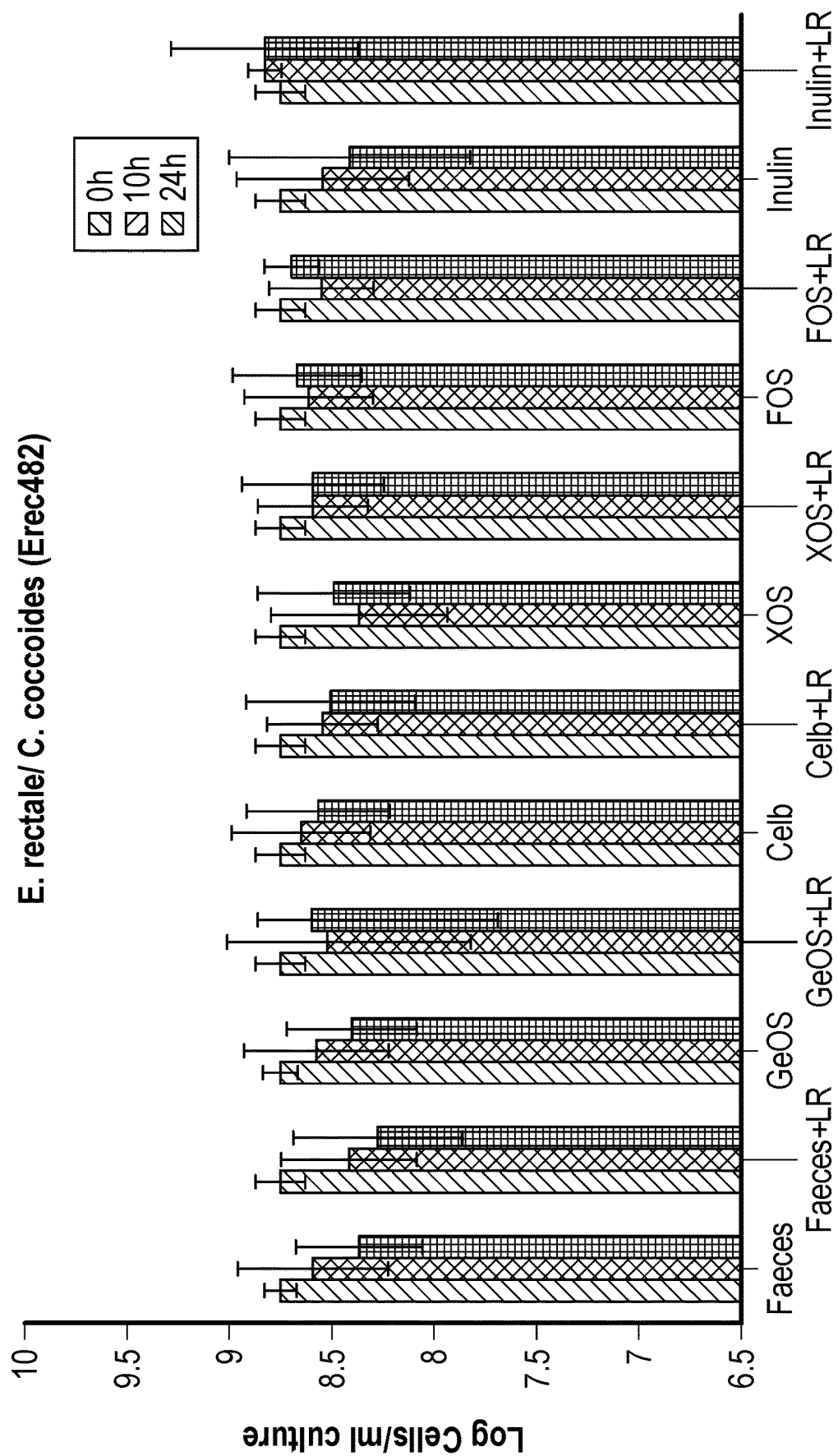
Figure 23:
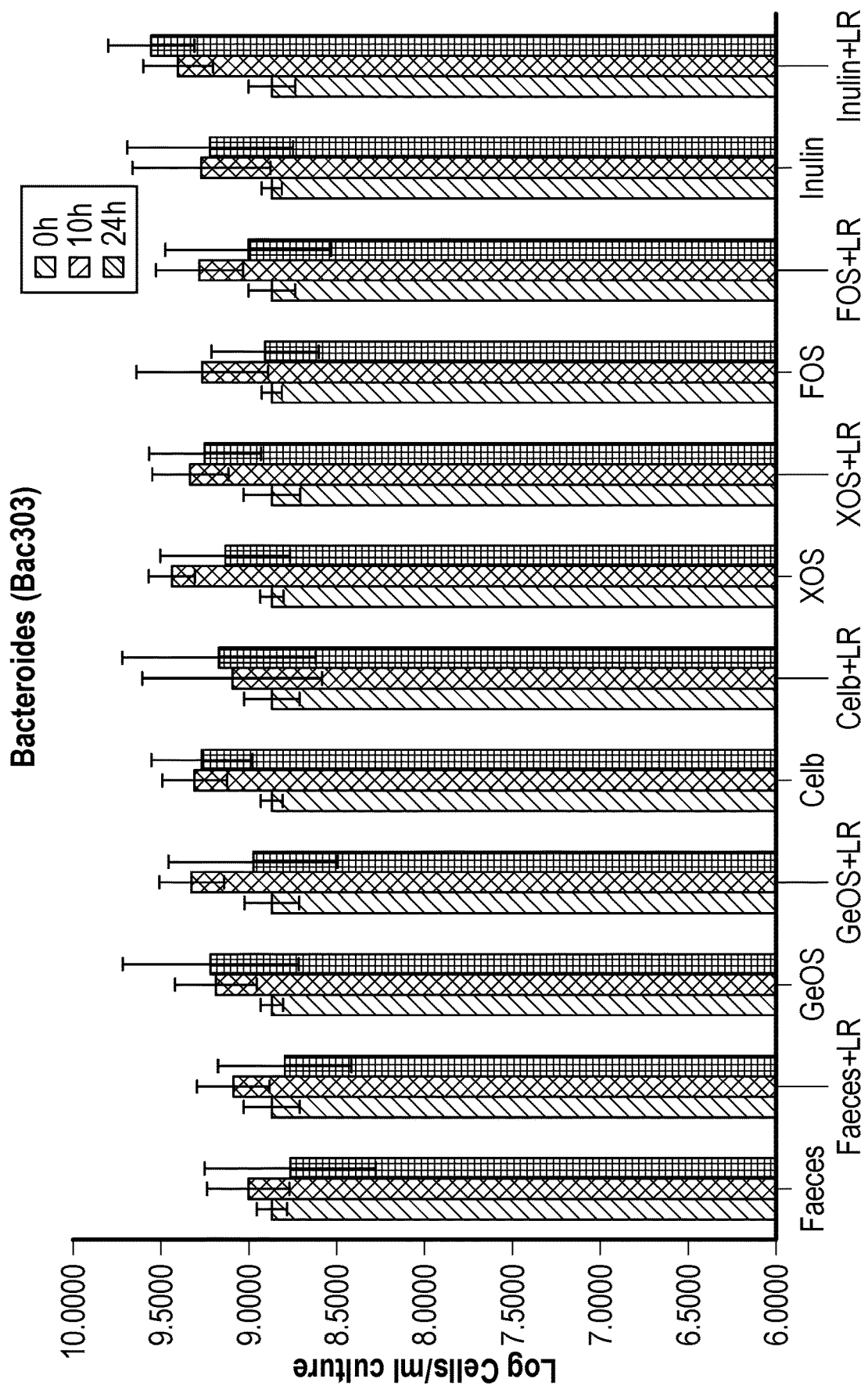
Figure 23:
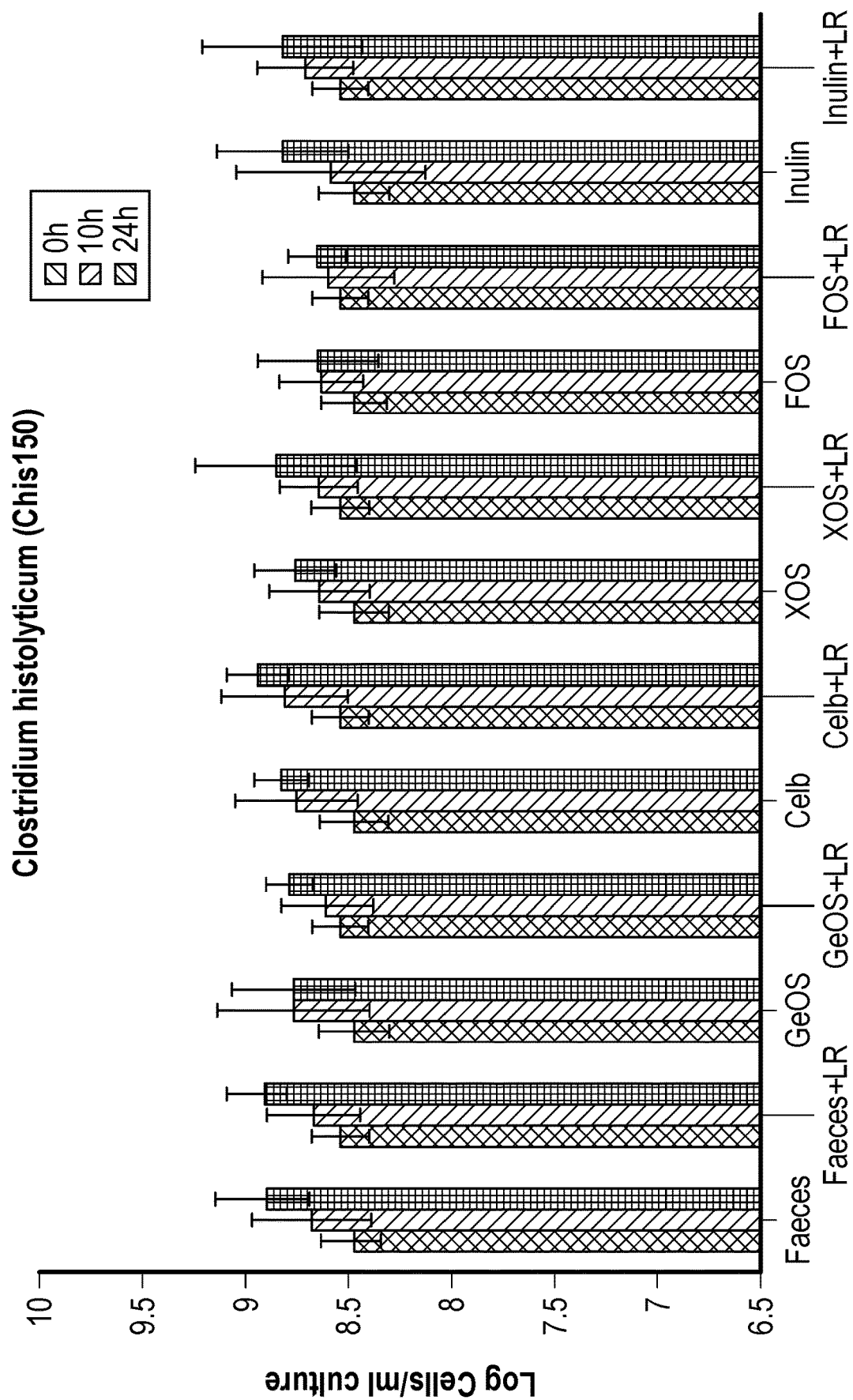
Figure 24:
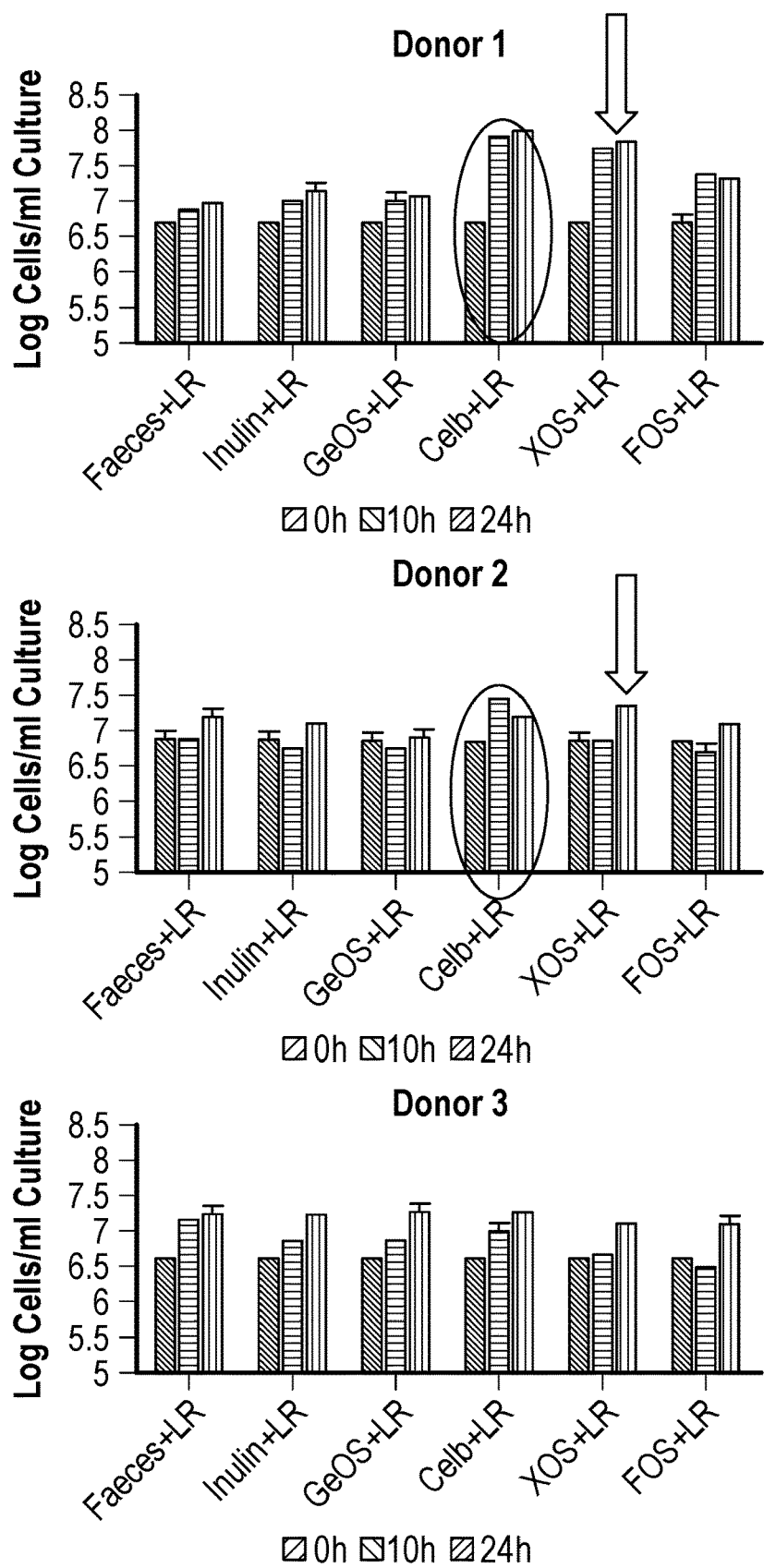
Figure 24:
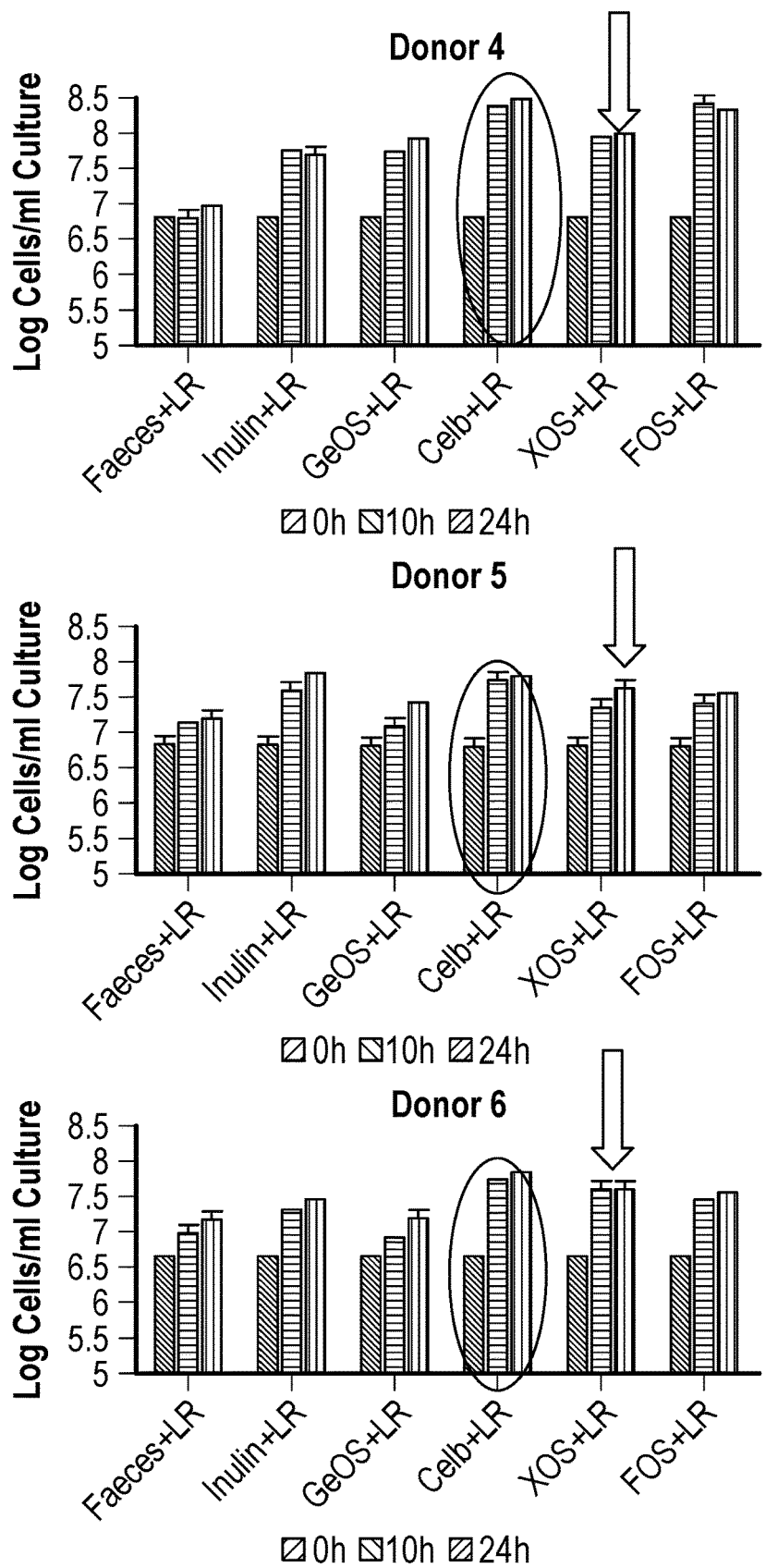
Figure 25:
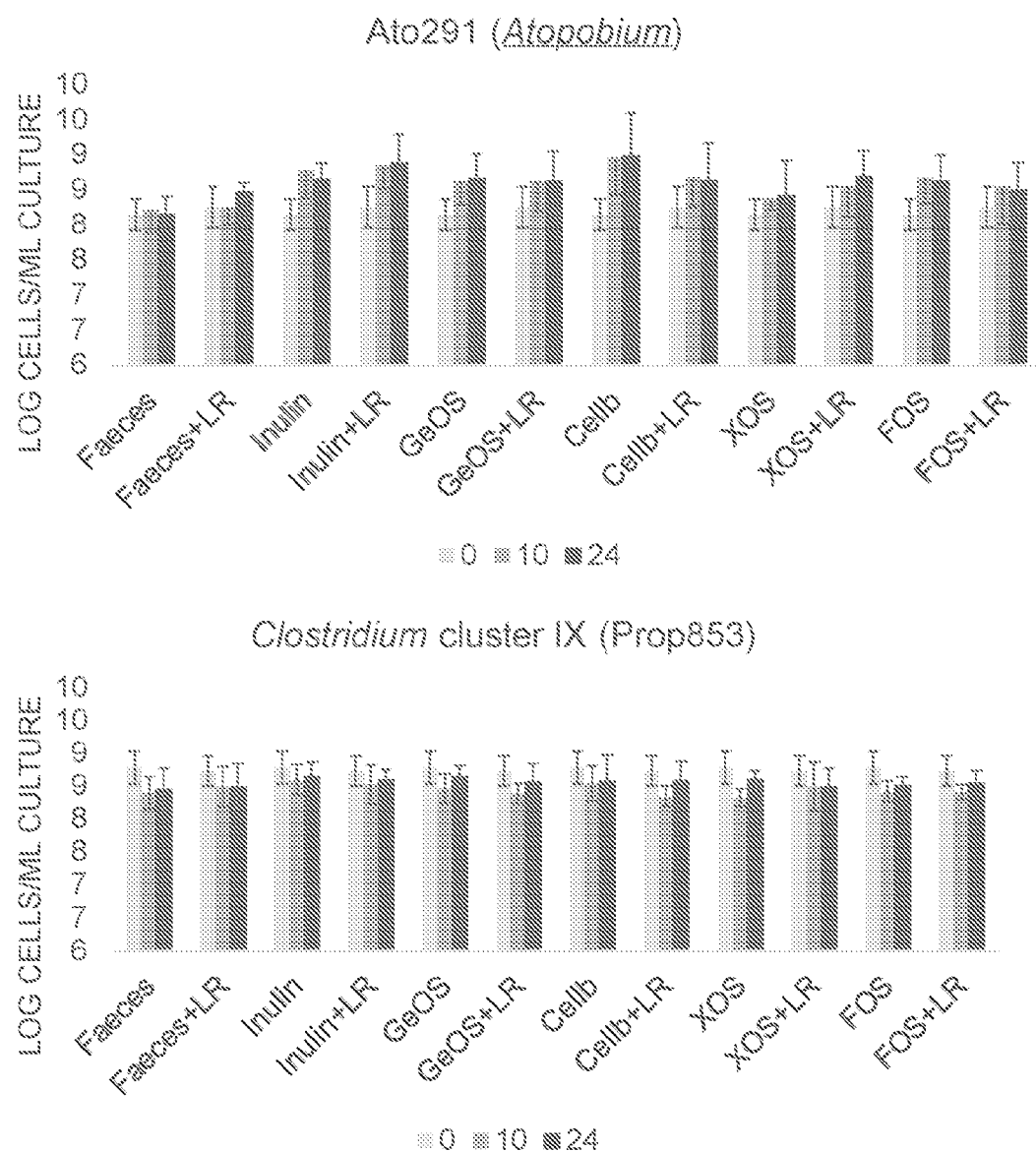
Figure 25:
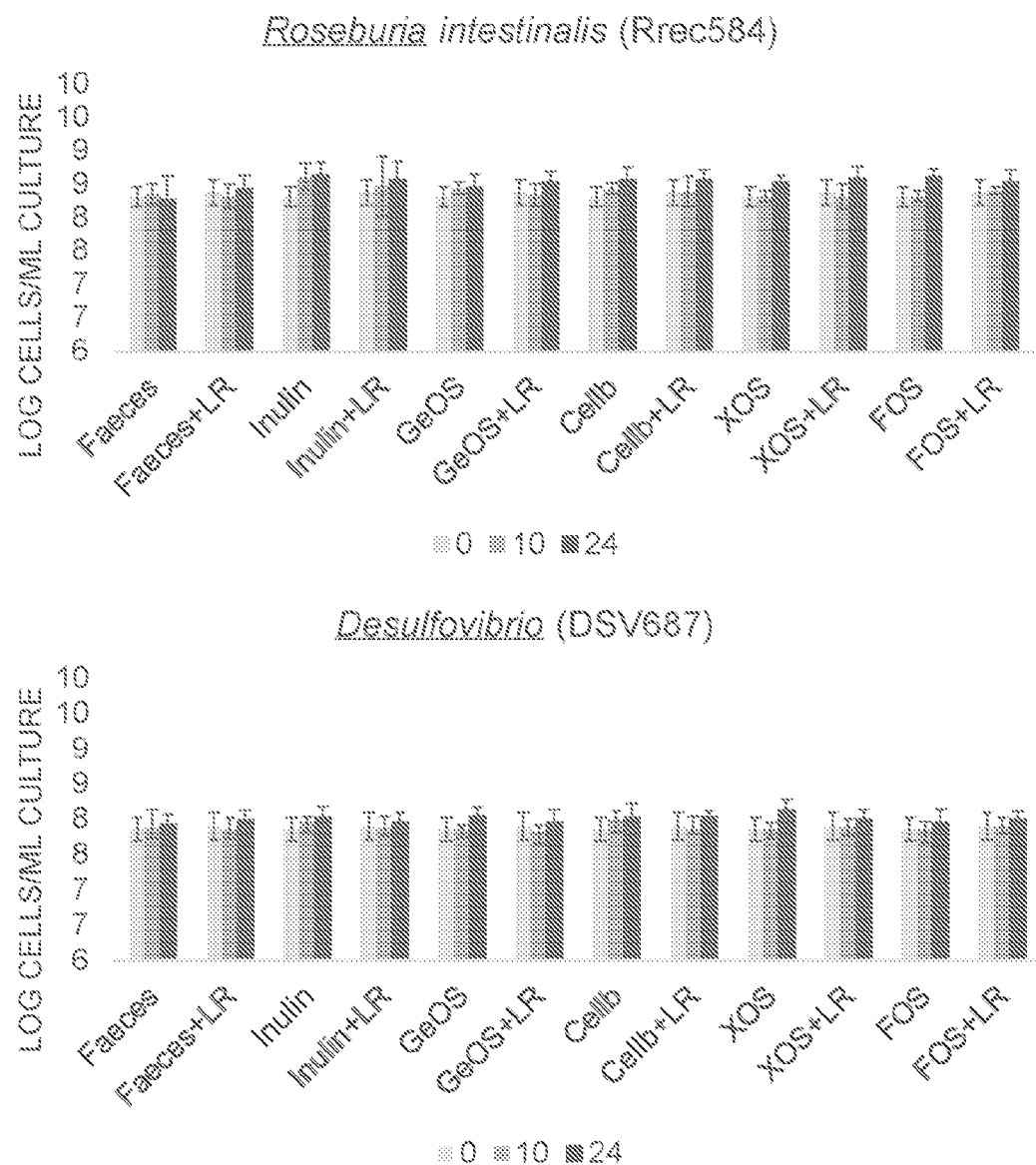
Figure 26:
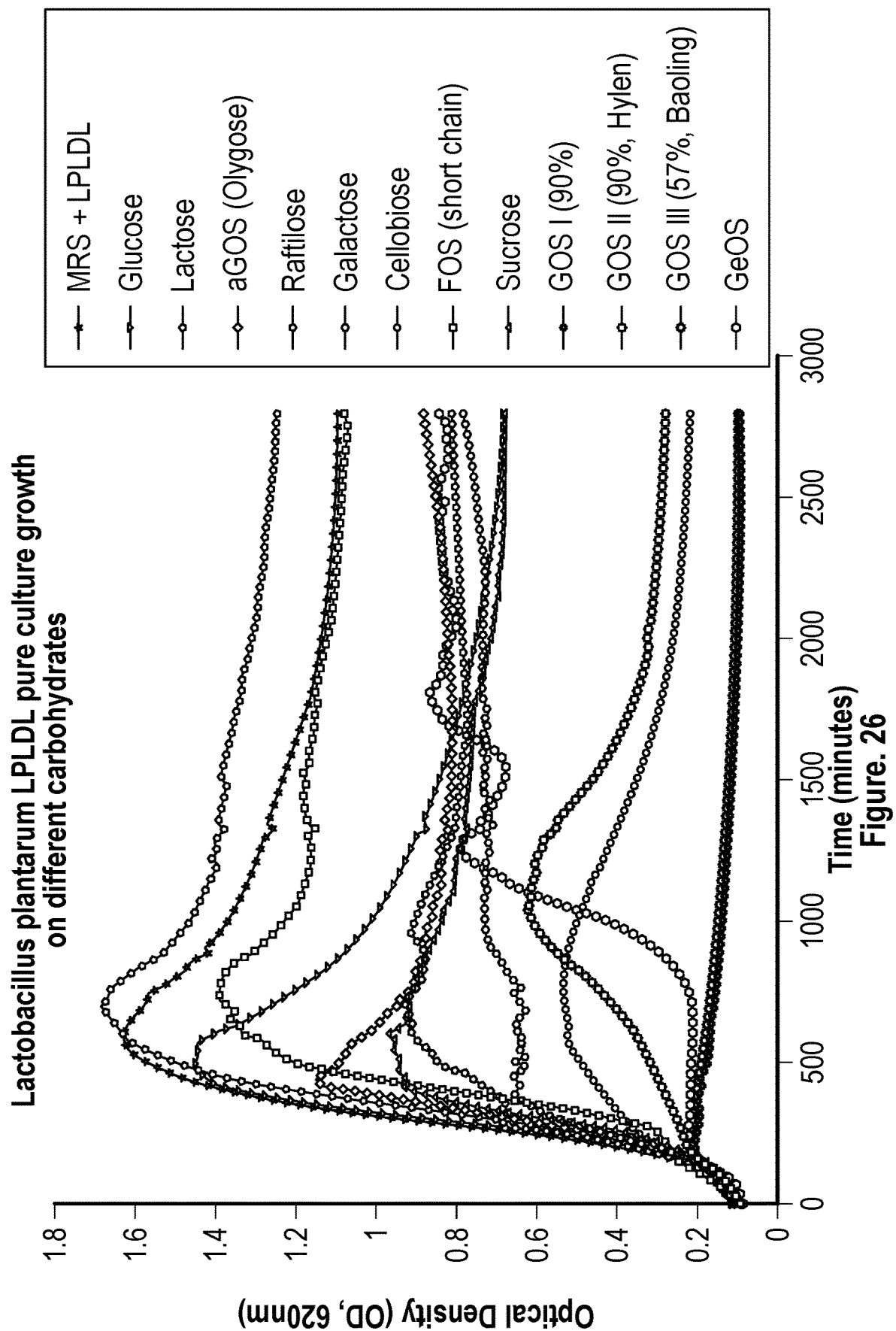

FIG. 8 is a graph showing growth rates ($\mu_{max}(h^{-1})$) for *L. rhamnosus* ATCC 53103 on Glucose; Sophorose; D-cellobiose; Gentiooligosaccharides; and Laminarobiose;

FIG. 9 is a graph showing the growth curves (OD, 620 nm) for *L. rhamnosus* ATCC 53103 on Gentiooligosaccharides; D-cellobiose; Sophorose; and Laminarobiose;

FIG. 10 is a graph showing the pure culture growth of *L. rhamnosus* ATCC 53103 in modified MRS broth (1% w/v glucose content substituted with the same amount of test carbohydrate (Cellobiose; Glucose; GeOS; XOS; Fructans: Inulin HP, OF P95, and Synergy 1);

FIG. 11A-11B are graphs showing cumulative gas determination for *L. rhamnosus* ATCC 53103 over 24 h non-pH controlled faecal fermentation with Inulin and Gentiooligosaccharides. Each graph, from left to right, shows three bars (prebiotic with faeces, prebiotic with faeces plus *L. rhamnosus* ATCC 53103-low dose, prebiotic with faeces plus *L. rhamnosus* ATCC 53103-high dose) relating to Donor 1, Donor 2, Donor 3, Donor 4, Donor 5 and Donor 6. *L. rhamnosus* ATCC 53103 was tested at two doses, $0.75 \times 10^4$ cfu (low) and $5.36 \times 10^4$ cfu (high) relevant to the number of viable *L. rhamnosus* ATCC 53103 delivered in the proximal colon ($10^6$CFU);

FIG. 11C-11D are graphs showing cumulative gas determination for *L. rhamnosus* ATCC 53103 over 24 h fermentation with Xylooligosaccharides and Cellobiose. Each graph, from left to right, shows three bars relating to Donor 1, Donor 2, Donor 3, Donor 4, Donor 5 and Donor 6;

FIG. 12A-12B are graphs showing the negative controls where (A) depicts faecal slurry and (B) depicts *L. rhamnosus* ATCC 53103 in faecal culture without carbohydrate source present. The graph in FIG. 11A, from left to right, shows three bars relating to Donor 1, Donor 2, Donor 3, Donor 4, Donor 5 and Donor 6;

FIG. 13 are graphs showing the rate of gas determination in faecal culture for each of six faecal donors: Inulin (black=Inulin, green=Inulin+LR Low dose, red=Inulin+LR High dose);

FIG. 14 are graphs showing the rate of gas determination in faecal culture for each of six faecal donors: Gentiooligosaccharides (black=Gentiooligosaccharides, green=Gentiooligosaccharides+LR Low dose, red=Gentiooligosaccharides+LR High dose);

FIG. 15 are graphs showing the rate of gas determination in faecal culture for each of six faecal donors: Cellobiose (black=Cellobiose, green=Cellobiose+LR Low dose, red=Cellobiose+LR High dose);

FIG. 16 are graphs showing the rate of gas determination in faecal culture for each of six faecal donors: Xylooligosaccharides (black=Xylooligosaccharides, green=Xylooligosaccharides+LR Low dose, red=Xylooligosaccharides+LR High dose);

FIG. 17 is a graph showing the average concentrations (Log cells/ml culture) of *L. rhamnosus* ATCC 53103 (LR; tested at high dose: $5.36 \times 10^4$ cfu) in 36 h anaerobic pH controlled faecal batch cultures, determined using quantitative Polymerase Chain Reaction (qPCR);

FIG. 18 are graphs showing *L. rhamnosus* ATCC 53103 (LR) growth in faecal culture; inulin; GeOS; Cellb; XOS and FOS and the impact on different donors in 36 h, anaerobic, pH controlled faecal batch cultures, determined using quantitative Polymerase Chain Reaction (qPCR);

FIG. 19 are graphs showing metabolite synthesis (short chain fatty acids (SCFA) and lactate) in 36 h, anaerobic pH control culture in the absence (prebiotics) and presence (synbiotics) of *L. rhamnosus* ATCC 53103 ($5.36 \times 10^4$ cfu) of: Lactate prebiotics; SCFA prebiotics; Lactate synbiotics; and SCFA synbiotics;

FIG. 20 shows FISH images of commensal bacterial populations in faecal culture using DAPI (total bacterial counts) and Bif164 (*Bifidobacterium*);

FIG. 21 is a graph showing the impact on commensal microbiota: *Lactobacillus/Enterococcus* (Lab158) in 36 h, anaerobic, pH controlled faecal culture in basal media containing faecal slurry; GeOS; Cellb; XOS; FOS; and Inulin in the presence and absence of *L. rhamnosus* ATCC 53103 (LR; $5.36 \times 10^4$ cfu) determined by fluorescent in situ hybridisation (FISH);

FIG. 22 shows the impact on commensal microbiota: *Bifidobacterium* (Bif164) in 36 h, anaerobic, pH controlled faecal culture in basal media containing faecal slurry; GeOS; Cellb; XOS; FOS; and Inulin in the presence and absence of *L. rhamnosus* ATCC 53103 (LR; $5.36 \times 10^4$ cfu) determined by fluorescent in situ hybridisation (FISH);

FIG. 23 shows the impact on commensal microbiota: Dominant bacterial groups (*E. rectale/C. coccoides* (Erec482); *Bacteroides/Prevotella* (Bac303); and *Clostridium histo/yticum* (Chis150));

FIG. 24 shows graphs illustrating individual responses of *L. rhamnosus* ATCC 53103 (LR) to cellobiose, gentiooligosaccharides (GeOS), xylooligosaccharides (XOS), inulin (Beneo HP) and FOS (Beneo P95) at 0, 10 and 24 h pH controlled faecal batch culture fermentation, determined by qPCR using LR specific primers;

FIG. 25 shows graphs bacterial concentrations in pH controlled anaerobic faecal cultures (Ato291 (Atopobium) *Clostridium* cluster IX (Prop853); *Roseburia intestinalis* (Rrec584); and *Desulfovibrio* (DSV687)) using faeces from each of six healthy adults where the bacterial concentrations were obtained using fluorescent in situ hybridisation (FISH); and FIG. 26 shows a graph of the growth of *Lactobacillus plantarum* 2830 (ECGC 13110402) on a range of substrates including, MRS+LP2830, Glucose, Lactose, aGOS (Olygose), Raffinose, Galactose, Cellobiose, FOS (short chain), Sucrose, GOSI, GOSII, GOSIII and GeOS.

EXAMPLE 1

Experiments were conducted to identify any prebiotics which could be used in a combination formulation to support and enhance the growth of *Lactobacillus rhamnosus* ATCC 53103 (herein after referred to as "LR" and also used interchangeably).

Initially, oligosaccharides or formulations specifically designed to selectively enhance the survival and activity of LR in the human gut were assessed. Experiments were conducted in a multi-phase approach, exploring existing prebiotics and other oligo and polysaccharides to generate synbiotic formulations for LR: (i) oligosaccharide screening of prebiotics and other oligo and polysaccharides in pure culture to support LR growth; (ii) in vitro assessment of consumer acceptability of the synbiotic in terms of the potential to mediate gas related side effects in 24 h faecal culture models; and (iii) in vitro determination of optimum probiotic dose to minimise gas related side effects in in vitro faecal culture model.

Synbiotic potential of the selected oligosaccharides/ blends was then to be determined in 24 h, anaerobic, pH and temperature controlled micro-scale faecal (10 ml working volume) faecal batch culture models.

The models had been optimised to work at 1% w/v test oligosaccharide concentration and carried out at pH6.8, which is relevant to the distal colon. Conditions in the distal colon (carbohydrate availability, very slow transit time) are more relevant to batch culture design. Fermentations were to be set up in parallel in identical conditions with the only variable being the test oligosaccharides. The following combinations were to be tested in each experimental run:
- Faeces (prebiotic negative control)
- Faeces+LR (synbiotic negative control)
- Faeces+LR+GeOS (gentiooligosaccharides)
- Faeces+LR+Cellb (cellobiose)
- Faeces+LR+XOS (xylooligosaccharides)
- Faeces+GeOS
- Faeces+Cellb
- Faeces+XOS
- Feces+inulin (positive prebiotic control for test prebiotics)
- Faeces+FOS (positive prebiotic control for test prebiotics)
- Faeces+LR+inulin (positive prebiotic control for test synbiotics)
- Faeces+LR+FOS (positive prebiotic control for test synbiotics)

All vessels, run in parallel, were to be inoculated with the same faecal sample and the experiment repeated using a faecal sample from each of six different healthy donors. Samples were to be obtained at inoculation (0 h) and then at 8 and 24 h of fermentation for: determination of LR levels in faecal culture using qPCR; and determination of the impact of each intervention on commensal faecal microbiome composition using FISH to ensure novel prebiotic will not be fermented by undesirable bacteria and ensure selectivity in a complex, competitive culture environment. Analysis targeted numerically dominant and functionally significant faecal bacterial groups including *Bacteroides, Clostridium, Eubacterium, Propionibacterium, Bifidobacterium, Lactobacillus, Faecalibacterium, Atopobium*, and *Desulfovibrio*.

Lastly, determination of faecal microbiome activity through organic acid (SOFA and lactate) measurement was to be conducted at each sampling point. Information will indicate potential fermentation rates of each novel prebiotic. Oligosaccharide Screening/Novel Synbiotic Formulation to Selectively Support LR Growth Commercially available prebiotics and other oligo and polysaccharides were first screened using a fast throughput automated growth culture system under anaerobic conditions to establish ability to support LR growth and define growth rates (1% w/v). The following test substrates had been initially identified for further consideration: Short chain fructooligosaccharides (scFOS), oligofructose P95 (FOS), Orafti ST, Orafti HP, Synergy 1, Bioecolians (glucooligosaccharides), gentiooligosaccharides, fucosyllactose, ß glucan (low/medium/high molecular weight; derived from oats), yeast ß glucan, arabinoxylan, xylooligosaccharides, caseinoglycomacropeptide (cgmp), raffinose, stachyose and Bio-Mos.

Substrates shown to be able to support LR growth at high growth rates were then selected for side effect determination. *Lactobacillus rhamnosus* ATCC 53103 Pure Culture Growth Screening on Commercially Available Oligo/Polysaccharides The aim of the experiment was to investigate the growth behavior of *L. rhamnosus* ATCC 53103 under a wide variety of commercially available, oligo and polysaccharides and to evaluate impact of test substrate physical characteristics on screening process and investigate growth on GOS synthesized by *L. rhamnosus* GR1 β-galactosidases. Results would be evaluated on the basis of: microbial growth (OD-Fermentation time); growth rate $[\mu_{max}(h^{-1})]$; and change in optical density (max-min). Growth preferences of *Lactobacillus rhamnosus* ATCC 53103 would be used to determine target structures and carbohydrates for use as prebiotics for *L. rhamnosus* species or strains.

LR was pre-grown on MRS solid and liquid media, and growth curve experiments were carried out in 96 well plates using modified MRS broth (no glucose present); glucose content substituted by 1% (w/v) of each of the test substrates. Three experimental repeats were carried out—each test conducted in triplicate for 48 h under anaerobic growth conditions. Negative control: modified MRS broth, modified MRS broth+lactose without carbohydrate source, MRS broth (quality control). Positive control: modified MRS+1% glucose+LR. Continuous optical density (OD) measurements were obtained under anaerobic conditions. A reducing agent was added to the modified MRS (L-cysteine HCl, 0.08 g/L) and an indicator of anaerobiosis (resazurin, 4 mL/L solution of 0.025 g/100 mL) was used to ensure anaerobic conditions. Microbial streaking on MRS petri dishes was carried out at the end of each experiment to exclude contamination.

Microbial Growth

As illustrated in FIGS. 1 to 8, all test substrates demonstrated average growth rates and yields with the exception of gentiooligosaccharides. The highest growth rates and yields were observed on gentiooligosaccharides, and xylooligosaccharides but not galactomannan.

The next phase was to evaluate cellobiose, laminaribiose and sophorose at 1% (w/v) substrate concentrations to further investigate *L. rhamnosus* ATCC 53103 preference for specific structures and the most promising substrates to be screened in faecal culture gas experiments under anaerobic conditions for 24 h.

High growth yields were achieved by all test di and oligo-saccharides as illustrated in FIG. 9. All disaccharides exhibit higher growth yields than gentiooligosaccharides. Cellobiose exhibits notably longer lag phase compared to all other test di- and oligo-saccharides. Clear indications of β-glucosidase activity was seen.

Rate of Gas Determination

The aims of this experiment were to determine: (i) the total gas production over a 24 h fermentation period of each of carbohydrate of interest; (ii) the kinetics of gas production (rate) to evaluate the potential of increased abdominal discomfort in vivo upon the ingestion of the carbohydrates of interest; and (iii) the impact of using the selected carbohydrates in combination with LR on total and rate of gas production.

Determination of rate of gas was of particular importance as gas generation at specific time points rather than continuously at low or moderate levels may correlate with abdominal discomfort in vivo and important in relevance to consumer acceptability.

The experiments investigated the potential for gastrointestinal discomfort in vitro, through the determination of rate of gas and cumulative gas production in faecal culture. The cultures were non-pH controlled and six experimental runs were conducted using faeces from six different healthy adults. Headspace gas readings collected every 3 h over a 24 h period for rate of gas determination The experimental design was as follows:
Faeces
Faeces+*L. rhamnosus* ATCC 53103 (negative control)
Faeces+Inulin HP (positive prebiotic control)
Faeces+Inulin HP+*L. rhamnosus* ATCC 53103 (positive synbiotic control)
Faeces+test carbohydrate
Faeces+test carbohydrate+*L. rhamnosus* ATCC 53103

*Lactobacillus rhamnosus* ATCC 53103 Test Dose Determination

Previous LR probiotic products were known to deliver $10^6$ cfu LR in the gut in vivo. Therefore, it was estimated that this would be equivalent to $10^6$ cfu in the proximal vessel ($V_1$=280 ml) of an in vitro, three stage continuous culture model of the human colon (gut model) as described by Gibson and Macfarlane (1998). This model has been validated to simulate growth substrate availability and luminal bacterial populations in the human gut. Interventions can be tested in directly relevant doses to those used in vivo in humans.

Intervention dose used in the non-pH controlled gas determination experiments and the pH controlled faecal batch culture experiments was calculated based on the relative amounts of faecal inoculum and LR viable counts in the gut model (low dose, $0.75 \times 10^4$ cfu) and the relative concentrations of total bacteria to LR viable counts in the gut model (high dose, $5.36 \times 10^4$ cfu). Both doses were tested in the non-pH controlled gas determination faecal cultures to determine the possible role of LR in rate and cumulative gas production.

The main test outcomes for these experiments were the impact of LR addition to culture at two different doses and the gas related side effect potential of the synbiotic relevant to inulin.

As shown in FIGS. 11A-11C, no dose effect relevant to LR observed in total gas production. No impact of LR addition on total gas production. There was also donor response variability to different test oligosaccharides. Donors 4 and 7 were seen to be sensitive to Inulin and gentiooligosaccharides, whereas Donor 5 was sensitive to inulin. Donors 4 and 7 were seen to be sensitive to xylooligosaccharides and cellobiose, donor 5 was sensitive to cellobiose. In general gas generated in anaerobic culture was due to the prebiotic component and not the probiotic and was not correlated to the growth and activity of LR.

FIGS. 12-16 show that there is no effect of LR dose on total gas and rate of gas profiles and no impact of LR addition on total gas and rate of gas production compared to the prebiotic alone. Combinations generating high total gas also exhibited high rates of gas production. Xylooligosaccharides and Gentiooligosaccharides were tolerated the best by the majority of donors.

The rate of gas and total gas profiles observed, indicated stimulation of the activity of gas producing members of the faecal microbiota either through cross-feeding or direct fermentation of the test substrates.

In Vitro Assessment of Synbiotic Efficacy in Faecal Culture

An in vitro assessment of synbiotic efficacy in faecal culture using a pH controlled, anaerobic, temperature controlled cultures. The cultures were inoculated with faecal slurry of each of 6 healthy adults. The combinations included:
Faeces (prebiotic negative control)
Faeces+LR (synbiotic negative control)
Faeces+LR+GeOS (gentiooligosaccharides)
Faeces+LR+Cellb (cellobiose)
Faeces+LR+XOS (xylooligosaccharides)
Faeces+GeOS
Faeces+Cellb
Faeces+XOS
Feces+inulin (positive prebiotic control for test prebiotics)
Faeces+FOS (positive prebiotic control for test prebiotics)
Faeces+LR+inulin (positive prebiotic control for test synbiotics)
Faeces+LR+FOS (positive prebiotic control for test synbiotics)

FIG. 17 shows real-time PCR determination of LR concentrations in anaerobic, pH control faecal culture slurries (TaqMan system, reactions performed in triplicate). Average concentrations suggest growth of LR in faecal culture on cellobiose and XOS. No commensal LR was detected in the prebiotic only cultures (data not shown).

The primers for the real-time PCR determination was as follows:

```
LR-F
                                         (SEQ ID No. 1)
Forward primer    GCCCTTAACAGCAGTCTTC LR-R
                                         (SEQ ID No. 2)
Reverse primer    GCCCTCCGTATGCTTAAACC LR-P
                                         (SEQ ID No. 3)
Probe             FAM- TGTTGATCAATCAGAGGAT-BHQ1
```

FIGS. 18-19 show *L. rhamnosus* ATCC 53103 (LR) growth in faecal culture; inulin; GeOS; Cellb; XOS and FOS and the impact on different donors and the comparative metabolite synthesis by *L. rhamnosus* ATCC 53103 of: Lactate prebiotics; SOFA prebiotics; Lactate synbiotics; and SOFA synbiotics.

Fluorescent in situ hybridisation (FISH) experiments were then conducted to investigate the impact on commensal gut microbiome bacterial populations in faecal culture and the fluorescently labelled micrographs are shown in FIG. 20. FISH is a fully quantitative methodology for determining bacterial concentrations at the genus and species level. Oligonucleotide probes targeted 16S rRNA and allowed for direct enumeration of whole bacterial cells in biological samples including non-cultivable cells. The cells are labelled with a fluorescent dye (Cy3) for visualisation by fluorescent microscopy.

Analyses of commensal bacterial populations: molecular probe specificity shown below in Table 1.

TABLE 1

| Probe name | Target species | Fermentation products |
|---|---|---|
| Bif164 | *Bifidobacterium* genus | A, L, e, f |
| Lab158 | *Lactobacillus-Enterococcus* | L |
| Bac303 | most Bacteroidaceae and Prevotellaceae, some Porphyromonadaceae | A, P, S |
| Chis150 | most of the *Clostridium histolyticum* group (*Clostridium* cluster I and II) | A, P, B, L, e |
| Ato291 | *Atopobium* cluster | A, L, f |
| Erec482 | most of the *Clostridium coccoides-Eubacterium rectale* group (*Clostridium* cluster XIVa and XIVb) | A, B, L |
| Prop853 | *Clostridium* cluster IX | P |
| Fpra655 | *Faecalibacterium prausnitzii* | B |
| Rrec482 | *Roseburia* genus (*E. rectale, R. intestinalis*) | B |
| DSV687 | *Desulfovibrio* | |

(Key: A: acetate, B: butyrate, P: propionate, S: succinate, L: lactate, f: formate, e: ethanol)

The variability in *Lactobacillus/Enterococcus* response between different faecal donors is shown in FIG. 21. Negative controls appear to stimulate concentration in certain cultures, whereas FIG. 22 shows that *Bifidobacterium* populations stimulated by all test oligosaccharides. The addition of LR did not appear to impact *Bifidobacterium* concentrations. Low variability in volunteer response was also seen.

FIG. 23 shows the impact on commensal microbiota: Dominant bacterial groups Erec482: high variability noted between faecal donors/trend for decrease observed. Bac303: some impact on *Bacteroides/Prevotella* noted with GeOS, Cellobiose and XOS however it is unlikely to be statistically significant when compared to positive/negative controls, Chis150: Identical patterns of increase noted in *Clostridium histolyticum* for all tests including the negative and positive controls. It is unlikely the observed effect was relevant to any of the test interventions.

The measurement of enzyme activity secreted by *Lactobacillus rhamnosus* was investigated for the trisaccharide fraction obtained using cellobiose as carbon source during enzymatic synthesis. FIG. 24 show graphs illustrating individual responses of *L. rhamnosus* ATCC 53103 to cellobiose, gentiooligosaccharides (GeOS), xylooligosaccharides (XOS), inulin (Beneo HP) and FOS (Beneo P95) at 0, 10 and 24 h pH controlled faecal batch culture fermentation, determined by qPCR using LR specific primers. Ellipses and arrows signify increases in cellobiose and XOS respectively, in each volunteer. The impact of the test carbohydrates on commensal *L. rhamnosus* ATCC 53103 was also investigated, however levels were below the detection limit at all time points (not shown). Five out of the six volunteers used for the culture showed an increase of *L. rhamnosus* ATCC 53103 concentrations upon fermentation of cellobiose and XOS;

pH controlled anaerobic faecal culture experiments were conducted using faeces from each of six healthy adults were undertaken and the bacterial concentrations obtained using fluorescent in situ hybridisation (FISH) and the results illustrated in FIGS. 13 to 23 and 27. The experiement shows a significant increase in Lab158 in particular with XOS, cellobiose and gentiooligosaccharides. More responders within the 6 faecal donors responding with cellobiose and XOS compared to the positive controls (inulin and FOS). No significant impact was seen on *Bacteroides* and significant increases in *Bifidobacterium* with all test combinations. No significant impact of any of the treatments on Erec482 and Chis150 cells compared to the positive and negative controls. As shown in FIG. 25, some increases observed in Ato291 concentrations with inulin and cellobiose, but no significant impact on Prop853, Rrec584 and DSV687 levels.

Conclusions

*Lactobacillus rhamnosus* ATCC 53103 has very narrow carbohydrate utilisation preferences and can grow in pure culture on beta glucooligosaccharides such as cellobiose. XOS, GeOS and cellobiose. The rate and cumulative gas production were comparable to that of inulin and as such are unlikely to generate severe gas related side effects in vivo.

Cellobiose, was identified to be the best growth substrate for LR, as determined in pH controlled faecal batch cultures and mediated increases in LR concentration and activity (organic acid synthesis). XOS showed similar efficacy. This effect was not dependent on faecal donor enterotype, which implies direct fermentation of cellobiose and XOS by LR and not stimulation of LR through cross feeding.

For the fructans, the effect was volunteer dependent and implies the necessity of cross-feeding relationships to generate fermentable substrates for LR. LR in pure culture showed poor growth on fructans indicating that LR cannot directly grow on fructans (FIG. 10), it requires the fermentation activity of other species/genera the presence of which depends on each individual's commensal microbiome.

All test prebiotics stimulated *Bifidobacterium* populations, key bacteria in promoting a healthy gut environment. No effect was seen on *Eubacterium rectale/Clostridium coccoides, Clostridium histolyticum* or *Bacteroides, Desulfovibrio* and *Propiobibacterium* (*Clostridium* cluster IX). However analysis of SOFA profiles does not suggest an impact in these groups. Overall, no impact was observed on health negative bacterial groups.

The systematic screening program has identified two oligosaccharides (XOS/Cellobiose) which have high potential to selectively stimulate growth/activity of *Lactobacillus rhamnosus* ATCC 53103 (LR) in the GI tract.

The experiments showed the potential of cellobiose and XOS to enhance the numbers and activity of LR in faecal cultures.

EXAMPLE 2

Similar growth experiments to Example 1 above were conducted on *Lactobacillus plantarum* 2830 (ECGC 13110402) on a range of substrates including, MRS+LP, Glucose, Lactose, LP GOS, alphaGOS (a proprietary GOS product), Raffinose, Galactose, Cellobiose, FOS (short chain), Sucrose, GOS I (a proprietary GOS product), GOS II (a proprietary GOS product), GOS III (a proprietary GOS product) and Gentiooligosaccharides (GeOS).

FIG. 26 shows growth of *Lactobacillus plantarum* LP-LDL in modified MRS media, whereby the glucose (1% wt/vol) has been substituted with each of a of a selection of carbohydrate sources, to evaluate its capacity to support LPLDL. Experiments were carried out under anaerobic conditions on a 96-well microtiter plate system (FLUOstar Omega, BMG LABTECH) in a final volume of 200 μL using an inoculum size 10% (w/v), previously diluted to obtain an initial OD620 nm=0.2. Incubation was conducted under anaerobic conditions at 37° C. with interval shaking at 500 rpm every 5 min. Optical density measurements at 620 nm were employed to assess microbial growth.

Out of the oligosaccharides tested (cellobiose, FOS, gentiooligosaccharides, alphaGOS, GOS I, II & III and raffinose) cellobiose, followed by FOS, GOS II and GeOS (gentiooligosaccharides) supported the highest growth rates but also the highest growth yields of LP-LDL in pure culture, indicating a strong potential to be used as synbiotics to support its growth and activity in vivo.

The forgoing embodiments are not intended to limit the scope of the protection afforded by the claims, but rather to describe examples of how the invention may be put into practice.

BIOLOGICAL DEPOSITS

The application refers to the following indications of deposited biological material:
Name: European Collection of Cell Cultures
Address: Public Health England Porton Down,
 National Collection of Type Cultures,
 PHE Culture Collections, Microbiological Services,
 Porton Down,
 Sailsbury,
 SP4 OJG
 United Kingdom
Sample deposited: *Lactobacillus plantarum* 2830.
Sample genus: *Lactobacillus*.
Sample species: *plantarum*.
Sample strain no.: 2830.
Date: 4 Nov. 2013
Accession Number: 13110402

---

---

The invention claimed is:

1. A synbiotic composition comprising:
 a probiotic component, the probiotic component comprising *Lactobacillus plantarum* 2830 and/or *Lactobacillus rhamnosus* GG; and
 a prebiotic component comprising a growth medium which is specific for the growth of the probiotic component, wherein the prebiotic growth medium comprises xylooligosaccharides, cellobiose, gentiooligosaccharides, or any combination thereof.

2. The synbiotic composition of claim 1, wherein the composition or growth medium comprises up to 1 g of xylooligosaccharides, cellobiose, gentiooligosaccharides, or any combination thereof.

3. The synbiotic composition of claim 1, wherein the *Lactobacillus* spp. is in an amount in the range of $10^5$ cfu/g to $10^{12}$ cfu/g.

4. The synbiotic composition of claim 1, wherein *Lactobacillus* spp. and/or the growth medium is encapsulated.

5. The synbiotic composition as claimed in claim 4, wherein the growth medium is used to encapsulate the *Lactobacillus* spp.

6. The synbiotic composition of claim 1, wherein composition is in the form of one or more capsules, tablets, or sachets.

7. The synbiotic composition of claim 1, wherein the composition is in the form of a drinkable liquid and/or powder format and/or can be mixed with a solid or liquid food stuff.

8. The composition as claimed in claim 1, wherein the composition increases the population of *Lactobacillus* spp. in the gut of an individual.

9. The composition as claimed in claim 8, wherein the population is at least partially an indigenous population of the individual.

\* \* \* \* \*